United States Patent
Uezono et al.

(10) Patent No.: US 11,234,747 B2
(45) Date of Patent: Feb. 1, 2022

(54) MEDICAL DEVICE, DEVICE STRUCTURES FOR DENTISTRY, FOR HEAD AND NECK SURGERY AND FOR ORTHOPEDIC SURGERY, AND METHOD FOR BONDING MEDICAL DEVICE TO BONE

(71) Applicant: National University Corporation Tokyo Medical and Dental University, Tokyo (JP)

(72) Inventors: Masayoshi Uezono, Tokyo (JP); Kazuo Takakuda, Tokyo (JP); Keiji Moriyama, Tokyo (JP); Shoichi Suzuki, Tokyo (JP)

(73) Assignee: National University Corporation Tokyo Medical and Dental University, Tokyo (JP)

( * ) Notice: Subject to any disclaimer, the term of this patent is extended or adjusted under 35 U.S.C. 154(b) by 0 days.

(21) Appl. No.: 15/553,269

(22) PCT Filed: Feb. 25, 2016

(86) PCT No.: PCT/JP2016/055713
§ 371 (c)(1),
(2) Date: Aug. 24, 2017

(87) PCT Pub. No.: WO2016/136913
PCT Pub. Date: Sep. 1, 2016

(65) Prior Publication Data
US 2018/0235682 A1    Aug. 23, 2018

(30) Foreign Application Priority Data
Feb. 25, 2015  (JP) .............................. JP2015-035844

(51) Int. Cl.
*A61B 17/86*   (2006.01)
*A61C 7/00*    (2006.01)
(Continued)

(52) U.S. Cl.
CPC .............. *A61B 17/864* (2013.01); *A61C 7/00* (2013.01); *A61C 8/0012* (2013.01);
(Continued)

(58) Field of Classification Search
CPC ..... A61B 17/864; A61B 17/68; A61B 17/688; A61B 2017/8655; A61B 17/844;
(Continued)

(56) References Cited

U.S. PATENT DOCUMENTS 5,120,223 A   6/1992 Weissman
5,344,457 A * 9/1994 Pilliar .................. A61C 8/0012
                                                     433/174
(Continued)

FOREIGN PATENT DOCUMENTS

AU    2014900596    *  2/2014 ............. A61B 17/84
CN    101366664 A      2/2009
(Continued)

OTHER PUBLICATIONS

Search Report in International Application No. PCT/JP2016/055713 dated Mar. 22, 2016, 4 pages.
(Continued)

*Primary Examiner* — Nicholas D Lucchesi
*Assistant Examiner* — Mirayda A Aponte
(74) *Attorney, Agent, or Firm* — Marshall, Gerstein & Borun LLP

(57) ABSTRACT

A medical device includes a shaft portion with a hollow shape and inflected portions or an exposed portion. The shaft portion is inserted into a cortical bone or penetrates through the cortical bone and is inserted to a position reaching a cancellous bone at an inner side of the cortical bone. The inflected portions are inflected to radial direction outer sides from one end portion of an axial direction of the shaft portion, and are exposed at a surface of the cortical bone.
(Continued)

The exposed portion includes a portion that extends to the radial direction outer side from the one end portion of the axial direction of the shaft portion, and is exposed at the surface of the cortical bone.

12 Claims, 19 Drawing Sheets

(51) Int. Cl.
*A61C 8/00* (2006.01)
*A61B 17/68* (2006.01)
*A61C 8/02* (2006.01)

(52) U.S. Cl.
CPC .......... *A61C 8/0022* (2013.01); *A61C 8/0039* (2013.01); *A61C 8/0096* (2013.01); *A61B 17/686* (2013.01); *A61B 2017/8655* (2013.01); *A61C 8/0006* (2013.01)

(58) Field of Classification Search
CPC ......... A61B 17/84; A61B 17/58; A61B 17/56; A61B 17/686; A61B 17/86; A61B 17/8685; A61B 17/8635; A61B 17/863; A61B 17/7062; A61B 17/7001; A61C 7/00; A61C 8/00; A61C 8/0006; A61C 8/0012; A61C 8/0022; A61C 8/0039; A61C 8/0096; A61C 13/225; A61C 8/0033; A61C 8/0018; A61C 8/0037; A61C 8/0093; A61F 2/442; A61F 2/44; A61F 2/28; A61F 2/26
USPC ..... 433/18; 606/53, 313, 303; 411/80.5, 508
See application file for complete search history.

(56) References Cited

U.S. PATENT DOCUMENTS

| | | | |
|---|---|---|---|
| 5,514,210 A | 5/1996 | Hirota et al. | |
| 6,126,663 A | 10/2000 | Hair | |
| 6,355,044 B1* | 3/2002 | Hair | A61B 17/688 606/326 |
| 8,168,151 B2 | 5/2012 | Tanaka et al. | |
| 8,974,506 B2 | 3/2015 | Wenger et al. | |
| 9,198,702 B2* | 12/2015 | Biedermann | A61B 17/8625 |
| 10,603,091 B2* | 3/2020 | Oldakowska | F16B 19/1081 |
| 2006/0235410 A1 | 10/2006 | Ralph et al. | |
| 2007/0231364 A1 | 10/2007 | Nishimoto et al. | |
| 2011/0060373 A1* | 3/2011 | Russell | A61B 17/0401 606/304 |
| 2015/0132353 A1 | 5/2015 | Kikuchi et al. | |
| 2016/0022386 A1* | 1/2016 | McDonald | A61C 8/0019 433/176 |
| 2017/0172711 A1 | 6/2017 | Yamamoto et al. | |

FOREIGN PATENT DOCUMENTS

| | | | | |
|---|---|---|---|---|
| DE | 19634698 C1 | | 4/1998 | |
| DE | 102013105040 A1 | | 11/2014 | |
| JP | 7-101708 | | 4/1995 | |
| JP | 7-222752 | | 8/1995 | |
| JP | 07222752 A | * | 8/1995 | ......... A61B 17/7098 |
| JP | 11-199209 | | 7/1999 | |
| JP | 2000-5298 | | 1/2000 | |
| JP | 2003-190271 A | | 7/2003 | |
| JP | 2004-057729 A | | 2/2004 | |
| JP | 2005-342157 A | | 12/2005 | |
| JP | 2006-296558 A | | 11/2006 | |
| JP | 2006-314760 A | | 11/2006 | |
| JP | 2011-177507 A | | 9/2011 | |
| JP | 5-008396 B2 | | 8/2012 | |
| JP | 2012-532006 A | | 12/2012 | |
| JP | 2013-509922 A | | 3/2013 | |
| JP | 5-218093 B2 | | 6/2013 | |
| JP | 2014-104121 A | | 6/2014 | |
| WO | WO-2013/157638 A1 | | 10/2013 | |
| WO | WO-2014/164923 A1 | | 10/2014 | |
| WO | WO-2015/125625 A1 | | 8/2015 | |

OTHER PUBLICATIONS

Written Opinion in International Application No. PCT/JP2016/055713 dated Mar. 22, 2016.
Extended European Search Report in EP Application No. 16755657.0 dated Oct. 15, 2018, 8 pages.
Office Action in JP Application No. 2020-039780 dated Apr. 7, 2020, 8 pages.
Office Action in JP Application No. 2020-039780 dated May 12, 2020, 8 pages.
Notice of Reasons for Rejection in JP Application No. 2020-114138 dated Apr. 20, 2021, 8 pages.

* cited by examiner

BEFORE INSTALLATION AFTER INSTALLATION

FIG. 7A
FIG. 7B
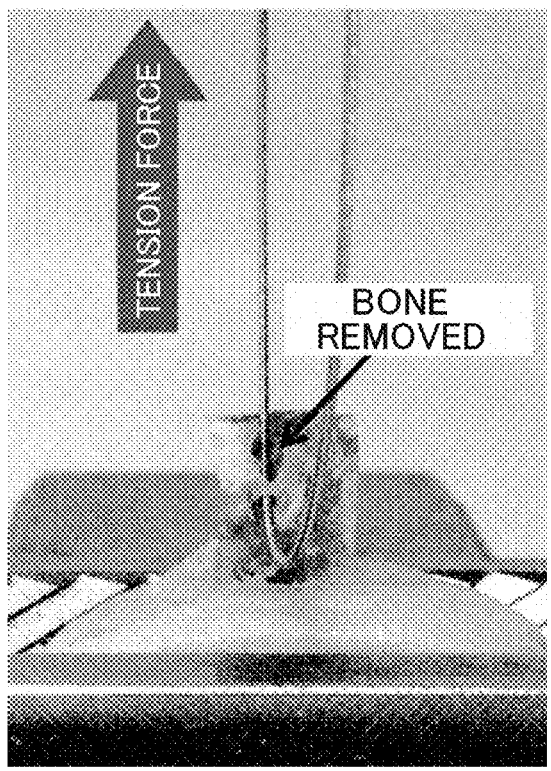
FRONT VIEW
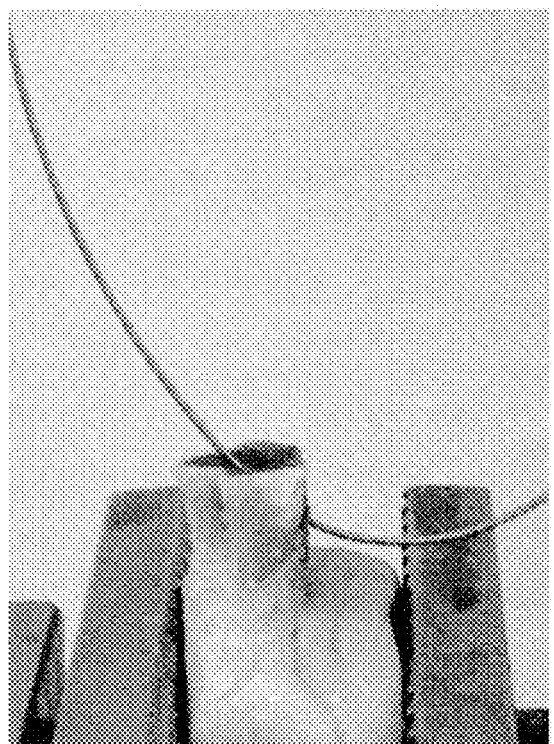
SIDE VIEW

FRONT VIEW

SIDE VIEW

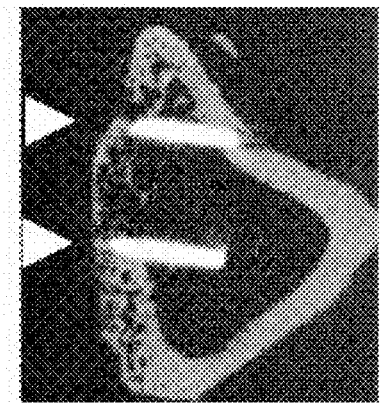
FIG. 10B (i)
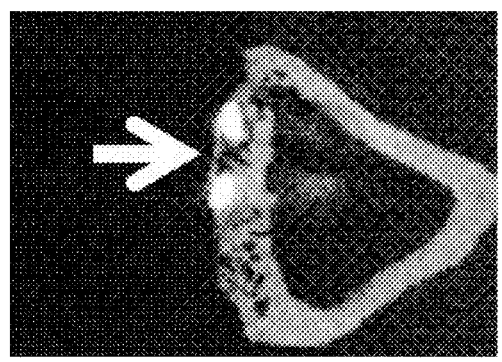
FIG. 10B (ii)
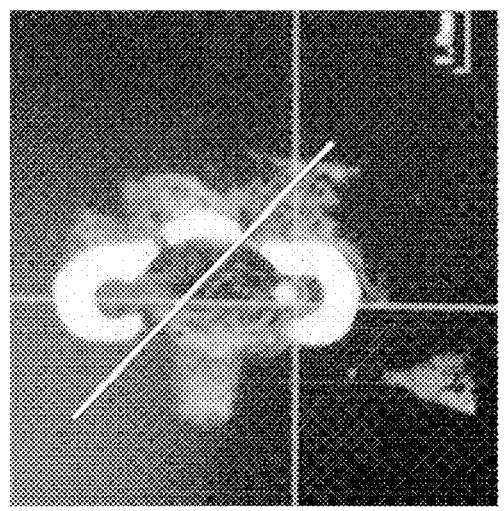
FIG. 10B (iii)

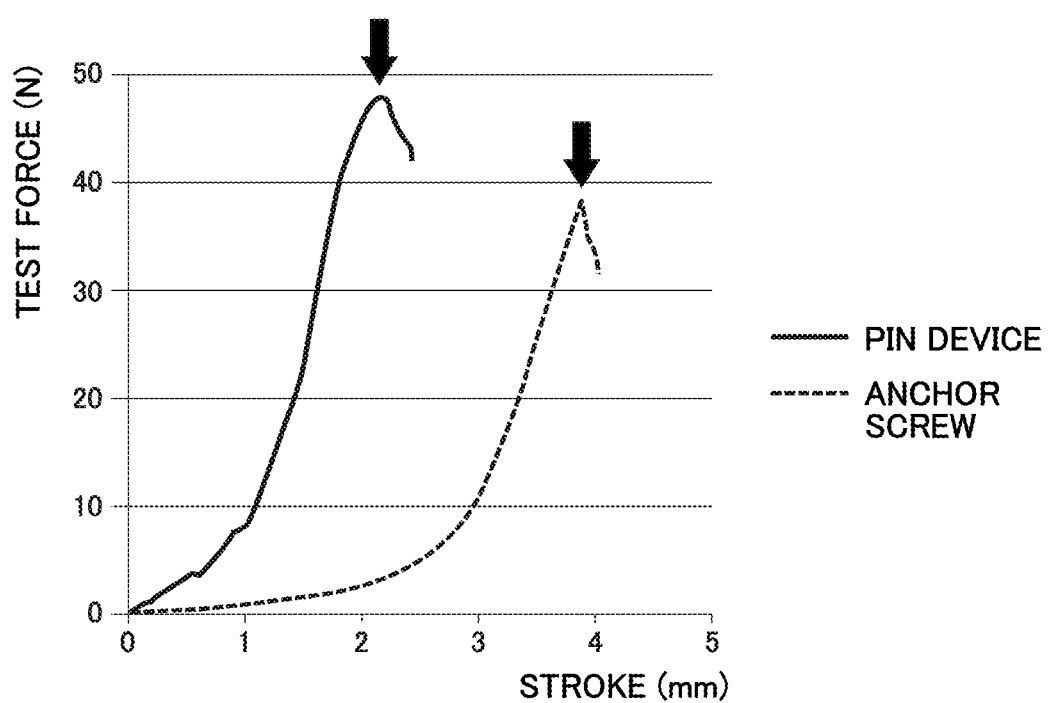

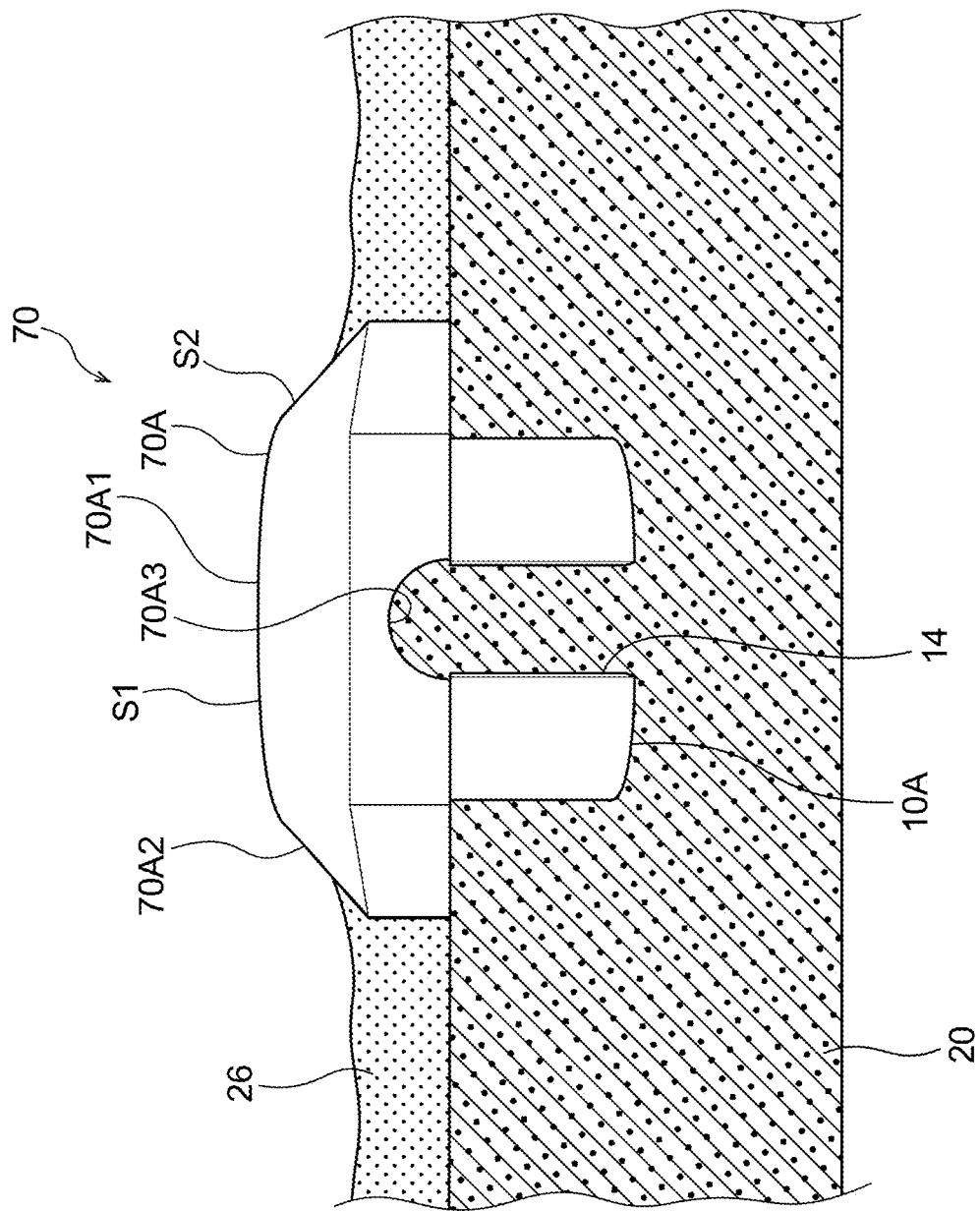

MEDICAL DEVICE, DEVICE STRUCTURES FOR DENTISTRY, FOR HEAD AND NECK SURGERY AND FOR ORTHOPEDIC SURGERY, AND METHOD FOR BONDING MEDICAL DEVICE TO BONE

TECHNICAL FIELD

The present invention relates to a medical device, to device structures for dentistry, for head and neck surgery and for orthopedic surgery, and to a method for bonding a medical device to bone.

BACKGROUND ART

Heretofore, implant devices for orthodontics have been proposed.

Japanese Patent Application Laid-Open (JP-A) No. 2004-57729 discloses an orthodontic implant (an implant device) provided with: an implant body, at an outer periphery of which a protruding thread is formed; and an anchor head that is fixed by a screw being screwed into an axial direction end portion of the implant body. In this orthodontic implant, a groove is provided between an end face of the implant body and the anchor head, two small screws are screwed into screw holes in the anchor head, and distal ends of the small screws project into the groove. A wire is disposed in the groove of the orthodontic implant. By adjustment of projection amounts of distal ends of the small screws, the wire is pressed by the distal ends of the small screws. Thus, the wire is fixed between the small screws and the end face of the implant body.

SUMMARY OF INVENTION

Technical Problem

However, in the structure recited in JP-A No. 2004-57729, a length of the orthodontic implant in the axial direction is specified to be long. More specifically, the length of the orthodontic implant is a dimension that is longer than the length of the screw (10.9 mm). Consequently, when the orthodontic implant is being screwed into and fixed in bone, a tooth root, tooth germ or the like may be damaged. Thus, there is scope for improvement.

The present invention has been devised in consideration of the circumstances described above. An object of the present invention is to provide a medical device that may implement secure bonding to bone with minimal invasion into a patient, device structures for dentistry, for head and neck surgery and for orthopedic surgery, and a method for bonding the medical device to bone.

Solution to Problem

A medical device according to a first aspect includes: a shaft portion with a hollow shape, the shaft portion being inserted into a cortical bone or the shaft portion penetrating through the cortical bone and being inserted to a position reaching a cancellous bone at an inner side of the cortical bone; and an inflected portion that is inflected to a radial direction outer side from one end portion of an axial direction of the shaft portion, the inflected portion being exposed at a surface of the cortical bone.

According to the invention according to the first aspect, the medical device is provided with the shaft portion with the hollow shape. The shaft portion is inserted inside the cortical bone, or the shaft portion penetrates through the cortical bone and is inserted to the position that reaches the cancellous bone at the inner side of the cortical bone. The medical device is also provided with the inflected portion that is inflected to the radial direction outer side from the one end portion of the axial direction of the shaft portion. In the state in which the shaft portion is inserted into the cortical bone or is inserted through the cortical bone to the position reaching the cancellous bone, the inflected portion is exposed at the surface of the cortical bone. Consequently, because the inflected portion touches against the surface of the cortical bone, subsidence of the shaft portion into inside of the bone is prevented. In this state, the cells with the bone-forming function migrate from the interior of the bone through the shaft portion with the hollow shape of the medical device, and new bone is formed at the inner face side of the shaft portion by these cells. Further, the cells with the bone-forming function migrate through the shaft portion with the hollow shape of the medical device to the surface of the cortical bone, and new bone is formed at the inflected portion. Thus, the medical device and the bone are more firmly joined. Therefore, the medical device may be firmly joined to the bone even with a short shaft portion.

The invention according to a second aspect is the medical device according to the first aspect in which one or more slits along the axial direction are provided at the shaft portion.

According to the invention according to the second aspect, because the one or two or more slits along the axial direction is/are provided at the shaft portion of the medical device, the outer diameter of the shaft portion deforms easily in directions of expansion and contraction, and the shaft portion may be more reliably fixed to the bone. In addition, the cells with the bone-forming function migrate from the interior of the bone through the slits of the shaft portion. Therefore, new bone may be formed rapidly by the cells at the inner face side of the shaft portion and the inflected portion.

The invention according to a third aspect is the medical device according to the first aspect or the second aspect in which the inflected portion includes a plural number of inflected portions provided in a circumferential direction of the shaft portion.

According to the invention according to the third aspect, because the inflected portion is provided in a plural number in the circumferential direction of the shaft portion, at least one or some of the inflected portions touch against the surface of the cortical bone. Therefore, subsidence of the shaft portion into inside the bone may be more reliably prevented.

The invention according to a fourth aspect is the medical device according to the second aspect or the third aspect in which an aperture portion is provided at a location of the inflected portion that is adjacent to the shaft portion, the aperture portion being continuous with the slit.

According to the invention according to the fourth aspect, because the aperture portion that is continuous with the slit is provided at the location of the inflected portion that is adjacent to the shaft portion, the outer diameter of the shaft portion may more easily deform in the directions of expansion and contraction, and the shaft portion may be more reliably fixed to the bone. In addition, the cells with the bone-forming function migrate from the interior of the bone through the aperture portion. Therefore, new bone may be formed rapidly by the cells at the inflected portion as well as at the inner face side of the shaft portion.

The invention according to a fifth aspect includes: a shaft portion with a hollow shape, the shaft portion being inserted into a cortical bone or the shaft portion penetrating through the cortical bone and being inserted to a position reaching a cancellous bone at an inner side of the cortical bone; and an exposed portion including a portion that extends to a radial direction outer side from one end portion of an axial direction of the shaft portion, the exposed portion being exposed at a surface of the cortical bone.

According to the invention according to the fifth aspect, the medical device is provided with the shaft portion with the hollow shape. The shaft portion is inserted inside the cortical bone, or the shaft portion penetrates through the cortical bone and is inserted to the position that reaches the cancellous bone at the inner side of the cortical bone. The medical device is also provided with the exposed portion including the portion that extends to the radial direction outer side from the axial direction one end portion of the shaft portion. In the state in which the shaft portion is inserted into the cortical bone or is inserted through the cortical bone to the position reaching the cancellous bone, the exposed portion is exposed at the surface of the cortical bone. Consequently, because the exposed portion touches against the surface of the cortical bone, subsidence of the shaft portion into inside the bone is prevented. In this state, the cells with the bone-forming function migrate from the interior of the bone through the shaft portion with the hollow shape of the medical device, and new bone is formed at the inner face side of the shaft portion by these cells. Thus, the medical device may be firmly joined to the bone with minimal invasion into the patient.

The invention according to a sixth aspect is the medical device according to the fifth aspect in which the one end portion of the shaft portion is closed off by a portion of the exposed portion, and at least a portion of a surface, at the opposite side of the exposed portion from the side thereof at which the shaft portion, is disposed is to be exposed from an epithelium that covers the cortical bone.

According to the invention according to the sixth aspect, in this structure the one end portion of the shaft portion is closed by the exposed portion. Thus, a surface area of the surface of the exposed portion at the opposite side thereof from the side at which the shaft portion is disposed may be increased. In the state in which the shaft portion is inserted inside the cortical bone or is inserted through the cortical bone to a position reaching the cancellous bone, at least a portion of the surface of the exposed portion at the opposite side thereof from the side at which the shaft portion is disposed is exposed from the epithelium covering the cortical bone. Hence, another medical device or the like may be joined to the portion of the surface at the opposite side of the exposed portion from the side at which the shaft portion is disposed that is exposed from the epithelium.

The invention according to a seventh aspect is the medical device according to the fifth aspect or the sixth aspect in which one or more slits along the axial direction are provided at the shaft portion.

According to the invention according to the seventh aspect, because the one or two or more slits along the axial direction is/are provided at the shaft portion of the medical device, the outer diameter of the shaft portion deforms easily in directions of expansion and contraction, and the shaft portion may be more reliably fixed to the bone. In addition, the cells with the bone-forming function migrate from the interior of the bone through the slits of the shaft portion. Therefore, new bone may be formed rapidly by the cells at the inner face side of the shaft portion.

The invention according to an eighth aspect is the medical device according to the sixth aspect or the seventh aspect in which a groove is provided at a location of a floor face of the exposed portion that is adjacent to the shaft portion, the groove being linked with the slit, opening at an inner face of the shaft portion, or a combination thereof.

According to the invention according to the eighth aspect, because the groove that is linked with the slit or opens to the inner face of the shaft portion is provided at the location of a floor face of the exposed portion that is adjacent to the shaft portion, the cells with the bone-forming function migrate from the interior of the bone through the aperture portion to the surface of the cortical bone. Therefore, new bone may be formed rapidly by the cells at the floor face and periphery of the exposed portion as well as at the inner face side of the shaft portion. Thus, the medical device and the bone are more firmly joined. Therefore, the medical device may be firmly joined to the bone even with a short shaft portion.

The invention according to a ninth aspect is the medical device according to any one of the first to eighth aspects in which a penetrating hole is formed at the shaft portion.

According to the invention according to the ninth aspect, the penetrating hole is formed at the shaft portion. Consequently, when the cells with the bone-forming function migrate through the penetrating hole, new bone is formed at peripheral edge portions of the penetrating hole. Thus, the medical device may be more firmly joined to the bone, in addition to which rotation of the medical device may be suppressed.

The invention according to a tenth aspect is the medical device according to any one of the first to ninth aspects in which a length of the shaft portion in the axial direction is specified such that at least 70% of the length is disposed in the cortical bone.

According to the invention according to the tenth aspect, because the length of the shaft portion in the axial direction is specified such that at least 70% of the length of the shaft portion is disposed in the cortical bone, damage to the bone may be suppressed compared to a case in which the shaft portion is inserted more deeply into the cancellous bone. Damage to a tooth root, tooth germ or the like may be suppressed more effectively than with, for example, a conventional orthodontic implant or the like in which around 5 mm or more of a shaft portion with a length of around 10 mm is inserted into cancellous bone.

The invention according to an eleventh aspect is the medical device according to any one of the first to tenth aspects in which a male thread portion is provided at an outer periphery face of the shaft portion.

According to the invention according to the eleventh aspect, the male thread portion is provided at the outer periphery face of the shaft portion, and the shaft portion is fixed in the bone by the male thread portion of the shaft portion being screwed into the bone. Therefore, the shaft portion may be more reliably fixed in the bone.

The invention according to a twelfth aspect is the medical device according to any one of the first to eleventh aspects in which the shaft portion and the inflected portion or exposed portion are formed of titanium or titanium alloy.

According to the invention according to the twelfth aspect, the shaft portion and the inflected portion or exposed portion are formed of titanium or a titanium alloy, which is excellent for biocompatibility.

The invention according to a thirteenth aspect is the medical device according to any one of the first to twelfth aspects in which a surface of the shaft portion and at least a portion of the inflected portion or exposed portion are coated with a biofunctional material.

According to the invention according to the thirteenth aspect, the surface of the shaft portion and the at least a portion of the inflected portion or exposed portion are coated with the biofunctional material, which can promote bonding between the medical device and the bone.

A device structure for dentistry, for head and neck surgery or for orthopedic surgery according to the present invention includes the medical device according to any one of the first to thirteenth aspects and employs the medical device to fix the device structure to the bone.

According to the device structure for dentistry, for head and neck surgery or for orthopedic surgery according to the present invention, cells with a bone-forming function rapidly migrate through the slit in the shaft portion, the aperture portion in the inflected portion, and/or the groove provided at the floor face of the exposed portion to the inner face side of the shaft portion with the hollow shape and the inflected portion or exposed portion exposed at the surface of the cortical bone. Therefore, new bone is rapidly formed by the cells at the inflected portion or the floor face and periphery of the exposed portion as well as at the inner face side of the shaft portion, and the medical device and bone are more firmly joined. Therefore, the medical device may be firmly joined to the bone even with a short shaft portion, and the medical device may be firmly joined to the bone with minimal invasion into the patient. When, for example, the medical device is used in fixing the device structure to bone for orthodontics, damage to a tooth root, tooth germ or the like may be suppressed more effectively than with a conventional orthodontic implant or the like in which around 5 mm or more of a shaft portion with a length of around 10 mm is inserted into cancellous bone.

A method for bonding a medical device according to the present invention is a method for bonding the medical device according to any one of the first to thirteenth aspects to bone, the method including, by fixing the shaft portion to the bone in a state in which the shaft portion is inserted into the cortical bone or the shaft portion penetrates through the cortical bone and is inserted to the position reaching the cancellous bone at the inner side of the cortical bone, and in a state in which the inflected portion or exposed portion is exposed at the surface of the cortical bone: allowing cells with a bone-forming function to migrate from inside the bone through the hollow shape of the shaft portion and the slit, allowing new bone to be formed by the cells at an inner face side of the shaft portion, and promoting bonding of the medical device to the bone; and allowing the cells with the bone-forming function to migrate from inside the bone to the surface of the cortical bone through the aperture portion that is provided at the location of the inflected portion adjacent to the shaft portion and that is continuous with the slit or the groove that is provided at the location of the floor face of the exposed portion adjacent to the shaft portion and that is linked with the slit or opens to the inner face of the shaft portion, allowing new bone to be formed by the cells at the inflected portion or the floor face and periphery of the exposed portion, and promoting bonding of the medical device to the surface of the cortical bone.

According to the method for bonding a medical device according to the present invention, the shaft portion of the medical device is inserted into the bone and the shaft portion is fixed in the state in which the inflected portion or exposed portion of the medical device is exposed at the surface of the cortical bone. Hence, the cells with the bone-forming function migrate through the slit in the shaft portion, the aperture portion in the inflected portion, and/or the groove provided at the floor face of the exposed portion to the inner face side of the shaft portion with the hollow shape and the inflected portion or exposed portion exposed at the surface of the cortical bone. New bone is formed by the cells at the inner face side of the shaft portion and the periphery of the exposed portion or inflected portion at the surface of the cortical bone, bonding the medical device to the bone. Therefore, the medical device may be firmly joined to the bone even with a short shaft portion, and the medical device may be firmly joined to the bone with minimal invasion into the patient.

A medical device according to the present invention may be fabricated by, for example, plastic working, cutting working or the like of a tube-shaped metal base material. A medical device according to the present invention may further be fabricated by casting the shape of the finished device. A medical device according to the present invention may still further be fabricated in the shape of the finished device by laminate production with a 3-D printer.

A metal constituting a medical device according to the present invention is not particularly limited; publicly known metal materials may be selected as appropriate in accordance with purposes and the like. With regard to biocompatibility, titanium or a titanium alloy is preferable. Titanium alloys that may be used include Ti—6Al—4V, Ti—6Al—4V ELI, Ti—6Al—7Nb, Ti—3Al-2.5V, Ti—5Al—2.5Fe and so forth.

A treatment such as etching, abrasive blasting, particle firing or the like may be applied to the surface of a medical device according to the present invention.

The surface of a medical device according to the present invention may be coated with a biofunctional material with a view to promoting bonding to bone. Hydroxyapatite (HAp), collagen (Col), and a HAp/Col complex of HAp and Col can be mentioned as biofunctional materials for coating medical devices according to the present invention. With regard to methods for fabricating the biofunctional materials mentioned above and coating the same onto metal surfaces, the materials and fabrication methods disclosed in JP-A Nos. 2006-314760, H7-101708, H11-199209, 2000-5298 and 2003-190271, International Publication No. 2013/157638, and so forth may be employed.

A medical device according to the present invention may be provided with a spongy composition formed of a biofunctional material (for example, Col or a HAp/Col complex) at the inner face side of the shaft portion. In this configuration, tissue fluid, blood and the like permeate into the spongy composition and the cells with the bone-forming function (osteogenic cells) migrate more easily. Moreover, the spongy composition serves as a scaffold, promoting division and differentiation of the osteogenic cells and bone formation. Hence, the bonding of the medical device of the present invention to the bone may be firmer. The spongy composition formed of the biofunctional material may be provided at the inner side face of the shaft portion of the present invention by adjustment of conditions in a method of coating of the metal surface.

In the method of bonding the medical device to bone according to the present invention, a spongy composition formed of a biofunctional material (for example, Col or a HAp/Col complex) may be inserted into the inner face side of the shaft portion of the medical device of the present invention and applied to an exposed face of the inflected portion after the medical device of the present invention has been installed in the bone.

Advantageous Effects of Invention

According to the present invention, the cells with the bone-forming function migrate through the slit in the shaft portion and aperture portion in the inflected portion, or groove provided at the floor face of the exposed portion to the inner face side of the shaft portion with the hollow shape and to the inflected portion or exposed portion exposed at the surface of the cortical bone, new bone is formed by the cells at the periphery of the inflected portion or exposed portion at the surface of the cortical bone as well as at the inner face side of the shaft portion, and the medical device is joined to the bone.

According to the present invention, the medical device may be firmly joined to the bone even with a short shaft portion, and the medical device may be firmly joined to the bone with minimal invasion into the patient.

BRIEF DESCRIPTION OF DRAWINGS

FIGS. 7A and 7B are photographs showing schematics of a mechanical test to check a bonding strength to bone of the device shown in FIGS. 6A and 6B.

FIGS. 10B (i), (ii), and (iii) are images (images reconstructed from micro-computed tomography) showing bone structure around inflected portions of the device according to the Example.

FIG. 11 is a graph showing results of the mechanical tests to check the bonding strengths to bone of the device according to the Example and the orthodontic anchor screw according to the Comparative Example.

FIG. 12C is a sectional diagram showing a state in which the device shown in FIG. 12A is joined to bone.

DESCRIPTION OF EMBODIMENTS

Herebelow, exemplary embodiments of the present invention are described in accordance with the drawings.

First Exemplary Embodiment

Figure 1:
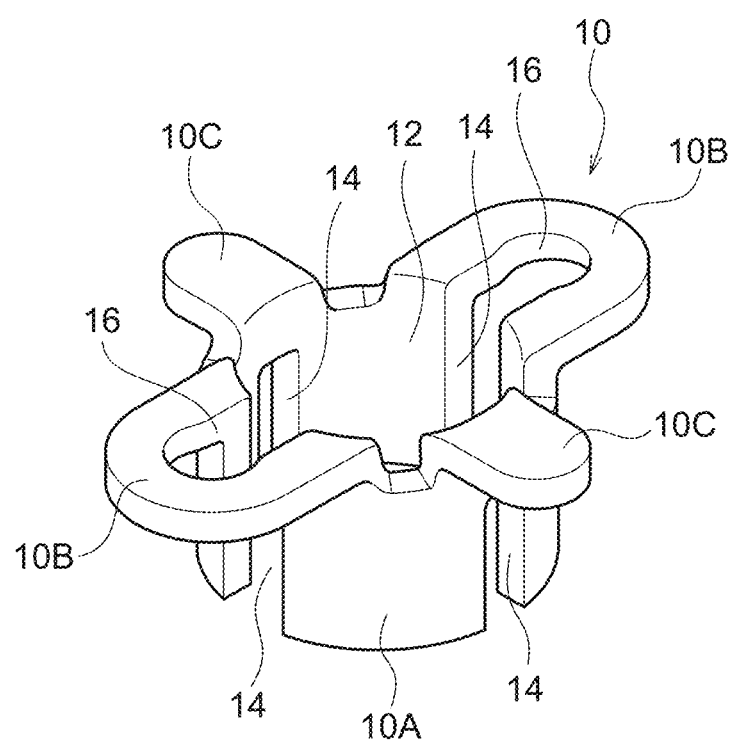
FIG. 1 is a perspective view showing a device that serves as a medical device according to a first exemplary embodiment of the present invention.
Figure 2A:
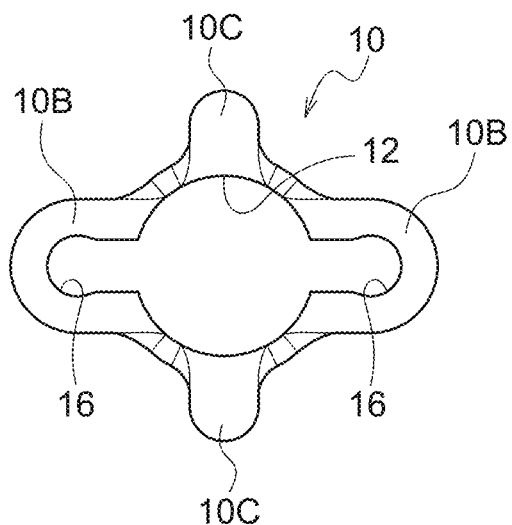
FIG. 2A is a plan view showing the device shown in FIG. 1.
Figure 2B:
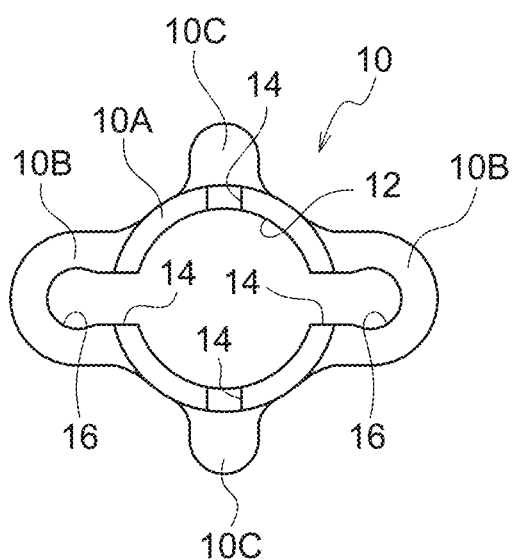
FIG. 2B is a bottom view showing the device shown in FIG. 1.

FIG. 1 is a perspective view showing a medical device (below referred to as "the device") according to a first exemplary embodiment of the present invention. FIG. 2A is a plan view (upper face view) showing the device shown in FIG. 1, and FIG. 2B is a bottom view (lower face view) showing the device shown in FIG. 1. As shown in FIG. 1 to FIG. 2B, a device 10 is provided with a shaft portion 10A with a hollow shape, and with flap-shaped inflected portions (outer flaps) 10B and 10C that are inflected to radial direction outer sides from one end portion of an axial direction of the shaft portion 10A. The inflected portions 10B and 10C serve as exposed portions. In other words, the device 10 is a pin-shaped device (which may below be referred to as "the pin device") equipped with the shaft portion 10A and a plural number of the inflected portions 10B and 10C.

In the present exemplary embodiment, the shaft portion 10A is formed in a substantially circular tube shape. A penetrating hole 12 is provided penetrating through a central portion at the inner side of the shaft portion 10A. A plural number of slits 14 along the axial direction are provided at the shaft portion 10A. Each slit 14 is formed over substantially the whole length in the axial direction of the shaft portion 10A. One length direction end of the slit 14 opens at a distal end of the shaft portion 10A. The slits 14 are disposed to be substantially equidistantly spaced in the circumferential direction of the shaft portion 10A. In the present exemplary embodiment, four of the slits 14 are arranged at positions approximately 90° apart in the circumferential direction of the shaft portion 10A. The shaft portion 10A is provided with four of the slits 14 along the axial direction. Therefore, the outer diameter of the shaft portion 10A may deform in directions of expansion and contraction.

A pair of the inflected portions 10B and another pair of the inflected portions 10C are provided at the one end portion of the axial direction of the shaft portion 10A. The inflected portions 10B are disposed at positions approximately 180° apart in the circumferential direction of the shaft portion 10A and extend in opposite directions away from one another. The inflected portions 10C are disposed between the pair of inflected portions 10B and extend in opposite directions away from one another. That is, a total of four of the inflected portions 10B and inflected portions 10C are provided. The inflected portions 10B and the inflected portions 10C are arranged alternately at positions approximately 90° apart in the circumferential direction of the shaft portion 10A.

A width of each inflected portion 10B (the width thereof in the circumferential direction of the shaft portion 10A) is specified to be larger than a width of each inflected portion 10C (the width thereof in the circumferential direction of the shaft portion 10A). An aperture portion 16 that is continuous with the slit 14 is provided at a location of each inflected portion 10B that is adjacent to the shaft portion 10A. The aperture portion 16 has a shape in plan view in which a portion with a rectangular shape is provided continuously from a portion with a substantially circular shape. A portion of the rectangular shape links with one end of the length direction of the slit 14. In the present exemplary embodiment, the length of the aperture portion 16 in a radial direction is specified to be longer than half of the length of the inflected portion 10B in the radial direction. The aperture portions 16 are provided only at the two inflected portions 10B and are not provided at the two inflected portions 10C. Because the aperture portion 16 that is continuous with the slit 14 is provided at the location of the inflected portion 10B that is adjacent to the shaft portion 10A, the outer diameter of the shaft portion 10A may deform easily in the directions of expansion and contraction.

The length of the shaft portion 10A in the axial direction is specified as a length to be inserted into cortical bone 22 structuring a bone 20 (see FIG. 3B), which is described below, or a length that penetrates through the cortical bone 22 and is inserted to a position that reaches cancellous bone 24 at an inner side of the cortical bone 22 (see FIG. 3B). The inflected portions 10B and inflected portions 10C project to radial direction outer sides from the shaft portion 10A. Thus, the inflected portions 10B and inflected portions 10C are structures that are exposed at the surface of the cortical bone 22 (see FIG. 3C) in the state in which the shaft portion 10A is inserted into the cortical bone 22 or the state in which the shaft portion 10A penetrates through the cortical bone 22 and is inserted to a position reaching the cancellous bone 24.

For example, if the device 10 is used for orthodontics, the length in the axial direction of the shaft portion 10A is set to around 2.0 mm. In the present exemplary embodiment, the outer diameter of the shaft portion 10A of the device 10 is set to around 2.4 mm, a thickness (plate thickness) of the shaft portion 10A and the inflected portions 10B is set to around 0.25 mm, and the inner diameter of the shaft portion 10A is said to around 1.9 mm. The dimensions of the device 10 described above do not limit dimensions of the present exemplary embodiment and may be modified. For example, if the shaft portion 10A of the device 10 is to be inserted only into the cortical bone 22, the length in the axial direction of the shaft portion 10A may be set to around 1.5 mm, substantially the same as a thickness of the cortical bone 22.

Furthermore, the number of the slits 14 in the shaft portion 10A of the device 10 is not limited by the number in the present exemplary embodiment and may be modified. For example, the number of the slits 14 in the shaft portion 10A may be one, and may be two or more. The numbers of the inflected portions 10B and inflected portions 10C and the positions of the inflected portions 10B and inflected portions 10C in the circumferential direction of the shaft portion 10A are also not limited by the present exemplary embodiment and may be modified.

In the present exemplary embodiment, the device 10 (the shaft portion 10A and the inflected portions 10B and 10C) is formed of titanium or a titanium alloy. Titanium alloys that may be used include Ti—6Al—4V, Ti—6Al—4V ELI, Ti—6Al—7Nb, Ti—3Al—2.5V, Ti—5Al—2.5Fe and so forth.

A metal constituting the device 10 is not limited to titanium or a titanium alloy; an alternative metal material may be selected as appropriate.

A treatment such as etching, abrasive blasting, particle firing or the like may be applied to surfaces of the device 10.

Surfaces of the device 10 (the shaft portion 10A and the inflected portions 10B and 10C) may be coated with a biofunctional material with a view to promoting bonding to bone. Hydroxyapatite (HAp), collagen (Col), and a HAp/Col complex of HAp and Col can be mentioned as biofunctional materials for coating the device 10.

The device 10 may be provided with a spongy composition formed of a biofunctional material (for example, Col or a HAp/Col complex) at the inner periphery face of the shaft portion 10A. In this configuration, tissue fluid, blood and the like permeate into the spongy composition and the cells with the bone-forming function (osteogenic cells) migrate more easily. Moreover, the spongy composition serves as a scaffold, promoting division and differentiation of the osteogenic cells and bone formation.

The device 10 according to the present exemplary embodiment may be fabricated by, for example, plastic working, cutting working or the like of a tube-shaped metal base material. The device 10 according to the present exemplary embodiment may further be fabricated by casting the shape of the finished device. The device 10 according to the present exemplary embodiment may still further be fabricated in the shape of the finished device by laminate production with a 3-D printer.

Now, operations and effects of the device 10, being a method of bonding the device 10 to bone, are described.

Figure 3A:
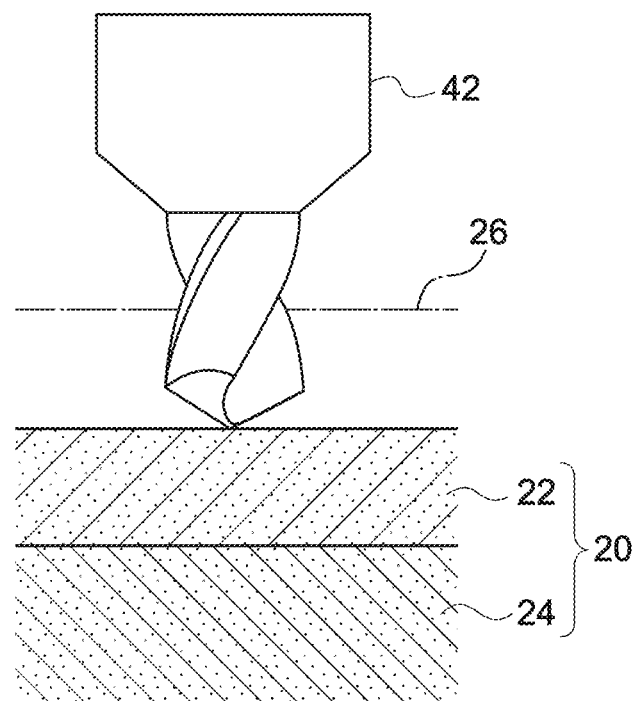
FIG. 3A is a sectional diagram of a method for bonding a device to bone, in which the device shown in FIG. 1 is joined to a bone, showing a state before a hole is formed at the bone.
Figure 3B:
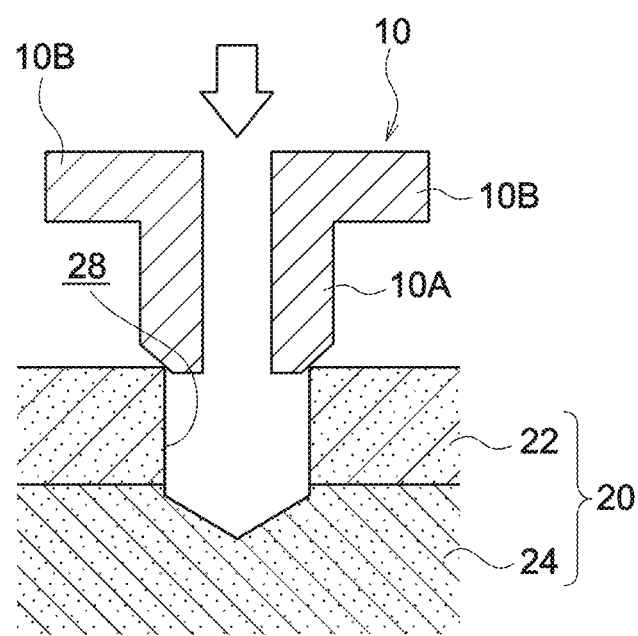
FIG. 3B is a sectional diagram of the method for bonding a device to bone, in which the device shown in FIG. 1 is joined to the bone, showing a step of fixing the device to the hole in the bone.

As shown in FIG. 3A, the bone 20 is provided with the cortical bone 22 at the surface side and the cancellous bone 24 at the inner side of the cortical bone 22. The surface of the cortical bone 22 is covered with a mucous membrane 26. Although not shown in the drawings, when the device 10 is to be fixed to the bone 20, the mucous membrane 26 is incised. In a state in which the mucous membrane 26 is lifted up, as shown in FIG. 3A, the bone 20 is cut into using a drill 42. Thus, a hole portion (a prepared hole) 28 is drilled (formed). The hole portion 28 has a length that penetrates into the bone 20 through the cortical bone 22 and reaches a little into the cancellous bone 24 (see FIG. 3B). During this drilling, it is desirable if an inner diameter of the hole portion 28 is set to be slightly smaller than the outer diameter of the shaft portion 10A of the device 10. Migration (mobilization) of cells with a bone-forming function (osteogenic cells) 30, which is described below, may be promoted by the hole portion 28 being formed with the length that reaches a little into the cancellous bone 24 (see FIG. 3C). The structure in the present exemplary embodiment is not limiting; the hole portion 28 may be provided only into the cortical bone 22 (not reaching the cancellous bone 24). The cells with a bone-forming function (osteogenic cells) 30 may migrate from inside the bone 20 in this configuration too.

Figure 3C:
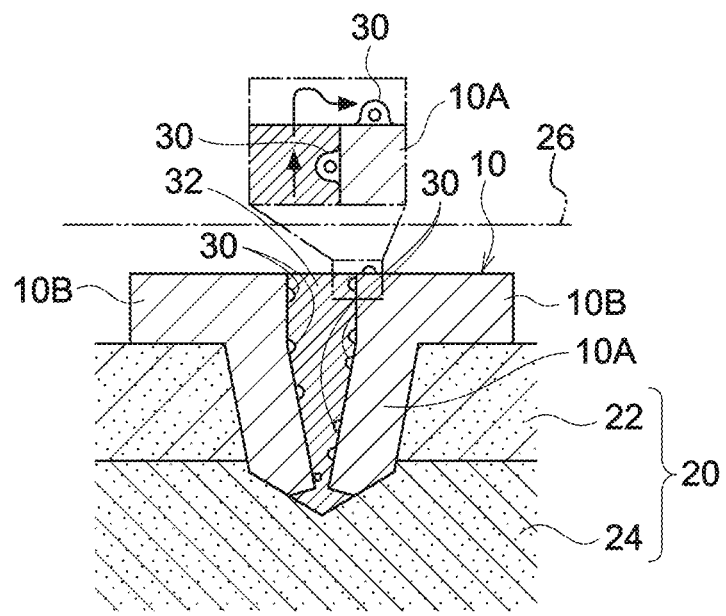
FIG. 3C is a sectional diagram of the method for bonding a device to bone, in which the device shown in FIG. 1 is joined to the bone, showing a state in which cells with a bone-forming function (osteogenic cells) are migrating through a shaft portion with a hollow shape of the device.

Then, as shown in FIG. 3C, the shaft portion 10A of the device 10 is inserted into the hole portion 28 in the bone 20. At this time, because the four slits 14 are provided along the axial direction of the shaft portion 10A, the outer diameter of the shaft portion 10A deforms in the direction of contraction and the shaft portion 10A can be inserted into the hole portion 28. The shaft portion 10A is pushed into the hole portion 28 until the inflected portions 10B and inflected portions 10C of the device 10 (see FIG. 1) touch against the surface of the cortical bone 22. Therefore, the shaft portion 10A is fixed in the hole portion 28 of the bone 20 in a state in which the inflected portions 10B and inflected portions 10C are exposed at the surface of the cortical bone 22. With this device 10, subsidence of the shaft portion 10A into inside the bone 20 may be prevented due to the inflected portions 10B and inflected portions 10C touching against the surface of the cortical bone 22.

It is desirable if at least 70% of the axial direction length of the shaft portion 10A of the device 10 is disposed in the cortical bone 22, preferably at least 80% of the same is disposed in the cortical bone 22, and more preferably at least 85% is disposed in the cortical bone 22. When at least 70% of the axial direction length of the shaft portion 10A is disposed in the cortical bone 22, an insertion length of the shaft portion 10A into the bone 20 is small and there may be relatively minimal invasion into the patient. In one example of the device 10, 100% of the axial direction length of the shaft portion 10A is disposed in the cortical bone 22, and in an alternative example, less than 100% but more than 95% of the axial direction length of the shaft portion 10A is disposed in the cortical bone 22.

In the present exemplary embodiment, the axial direction length of the shaft portion 10A is set to around 2.0 mm. Thus, the axial direction length of the shaft portion 10A is shorter than a conventional orthodontic implant or the like. Therefore, the shaft portion 10A is in a state of penetrating through the cortical bone 22 and being inserted to a position reaching a little into the cancellous bone 24 (see FIG. 3C). Therefore, when the device 10 is used in, for example, orthodontics, damage to a tooth root, tooth germ or the like may be suppressed more effectively than with a conventional orthodontic implant or the like in which around 5 mm or more of a shaft portion with a length of around 10 mm is inserted into cancellous bone.

In the present exemplary embodiment, the shaft portion 10A is in the state of penetrating through the cortical bone 22 and being inserted to a position reaching a little into the cancellous bone 24, but this structure is not limiting. Structures are possible in which the shaft portion 10A is inserted only into the cortical bone 22.

Figure 3D:
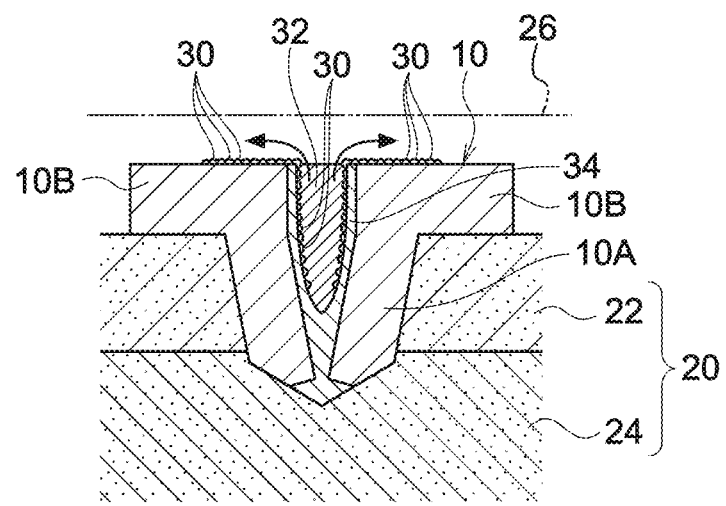
FIG. 3D is a sectional diagram of the method for bonding a device to bone, in which the device shown in FIG. 1 is joined to the bone, showing a state in which new bone is being formed at the shaft portion and inflected portions of the device by the cells with the bone-forming function (osteogenic cells).

Subsequently, the mucous membrane 26 is returned to its position before incision, covering over the device 10. In this state, when a predetermined duration passes, the cells with a bone-forming function (osteogenic cells) 30 migrate as shown in FIG. 3C from inside the bone 20 through the shaft portion 10A with the hollow shape, the slits 14 and the aperture portions 16 (see FIG. 1) of the device 10, to the side of the shaft portion 10A at which the inflected portions 10B and 10C are disposed, indicated by an arrow in blood 32. Hence, as shown in FIG. 3D, new bone 34 is formed by the migrating (mobilizing) cells 30 at the inner face side of the shaft portion 10A and at surfaces of the inflected portions 10B and 10C. That is, the inflected portions 10B and 10C of the device 10 serve as a platform for formation of the new bone 34 by the migrating cells 30 and fixing to the bone 20. As a result, the device 10 is firmly joined to the bone 20. At this time, because the new bone 34 is also formed at the aperture portions 16 of the inflected portions 10B of the device 10 (see FIG. 1), rotation of the device 10 may be suppressed.

In this device 10, because the hole portion 28 is formed with a length in the bone 20 that penetrates through the cortical bone 22 and reaches a little into the cancellous bone 24, and the shaft portion 10A of the device 10 is inserted into the hole portion 28, firm bonding of the device 10 to the bone 20 may be realized with minimal invasion into the patient.

Because the plural slits 14 along the axial direction are provided at the shaft portion 10A of the device 10 and the aperture portions 16 that are continuous with the slits 14 are provided at the inflected portions 10B, the outer diameter of the shaft portion 10A deforms easily in the directions of expansion and contraction. Therefore, the shaft portion 10A may be more reliably fixed in the bone 20. Moreover, because the cells with a bone-forming function 30 migrate from the interior of the bone 20 through the slits 14 of the shaft portion 10A and the aperture portions 16 of the inflected portions 10B, the new bone 34 may be formed rapidly by the migrating cells 30 at the inner face side of the shaft portion 10A and the surfaces of the inflected portions 10B and 10C.

In the present exemplary embodiment, the inner diameter of the hole portion 28 of the bone 20 is formed to be slightly smaller than the outer diameter of the shaft portion 10A of the device 10. Thus, the outer diameter of the shaft portion 10A is deformed in the direction of contraction and the shaft portion 10A is fixed in the hole portion 28. However, this structure is not limiting. For example, if the inner diameter of the hole portion 28 of the bone 20 is formed to be slightly larger than the outer diameter of the shaft portion 10A of the device 10, the outer diameter of the shaft portion 10A may be deformed in the direction of expansion such that the shaft portion 10A is fixed in the hole portion 28.

The hole portion may be formed to a length that reaches only into the cortical bone 22 (a length that does not reach into the cancellous bone 24), and the shaft portion 10A of the device 10 may be inserted into this hole portion. With a structure in which the shaft portion 10A of the device 10 is inserted only into the cortical bone 22, there is even less invasiveness into the patient. Moreover, in this structure, the cells with a bone-forming function (osteogenic cells) 30 may migrate from inside the bone 20 and the new bone 34 may be formed by the migrating cells 30 at the inner face side of the shaft portion 10A and the surfaces of the inflected portions 10B and 10C.

Second Exemplary Embodiment

Figure 4:
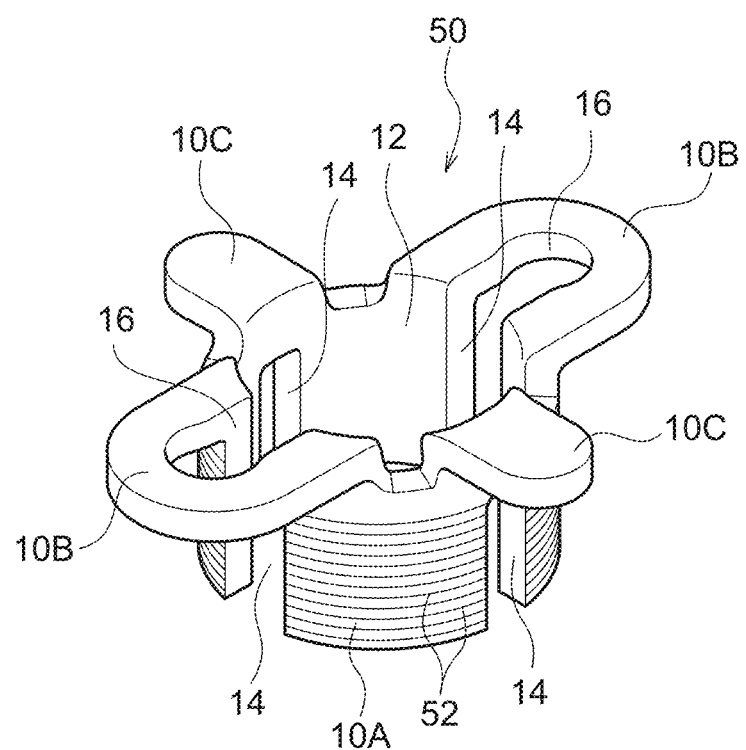
FIG. 4 is a perspective view showing a device that serves as a medical device according to a second exemplary embodiment of the present invention.

Now, a second exemplary embodiment of the medical device according to the present invention is described using FIG. 4. Structural elements, members and the like of the second exemplary embodiment that are the same as in the first exemplary embodiment are assigned the same reference numerals and are not described in detail.

As shown in FIG. 4, a device (a medical device) 50 is provided with the shaft portion 10A with the hollow shape, and a male thread portion 52 is provided at an outer periphery face of the shaft portion 10A. Other structures of the device 50 are the same as in the device 10 according to the first exemplary embodiment. In this device 50, four of the slits 14 are provided along the length direction of the shaft portion 10A. The device 50 may be fabricated by, for example, forming the male thread portion 52 at the outer periphery face of the circular tube-shaped shaft portion 10A and then forming the slits 14. However, a fabrication process of the device 50 is not limited to this process and may be an alternative process.

In this device 50, the hole portion 28 is formed at the bone 20 (see FIG. 3B) to be slightly smaller than the outer diameter of the male thread portion 52 of the shaft portion 10A (see FIG. 3B), after which the male thread portion 52 of the shaft portion 10A is screwed into the hole portion 28 in the bone 20. Thus, a thread groove is cut into peripheral edge portions of the hole portion 28 of the bone 20 and the shaft portion 10A is fixed to the bone 20. In this state, the cells with a bone-forming function 30 migrate from inside the bone 20 through the shaft portion 10A with the hollow shape, the slits 14 and the aperture portions 16 of the device 50, and the new bone 34 is formed by the migrating cells 30 at surfaces of the shaft portion 10A and the inflected portions 10B and 10C (see FIG. 3D).

In this device 50, firm initial fixing of the device 50 to the bone 20 (see FIG. 3D) may be implemented with minimal invasion into the patient. Moreover, because the shaft portion 10A is fixed to the bone 20 by the male thread portion 52 of the shaft portion 10A being screwed into the hole portion 28 in the bone 20, the shaft portion 10A may be reliably fixed to the bone 20.

Third Exemplary Embodiment

Figure 5:
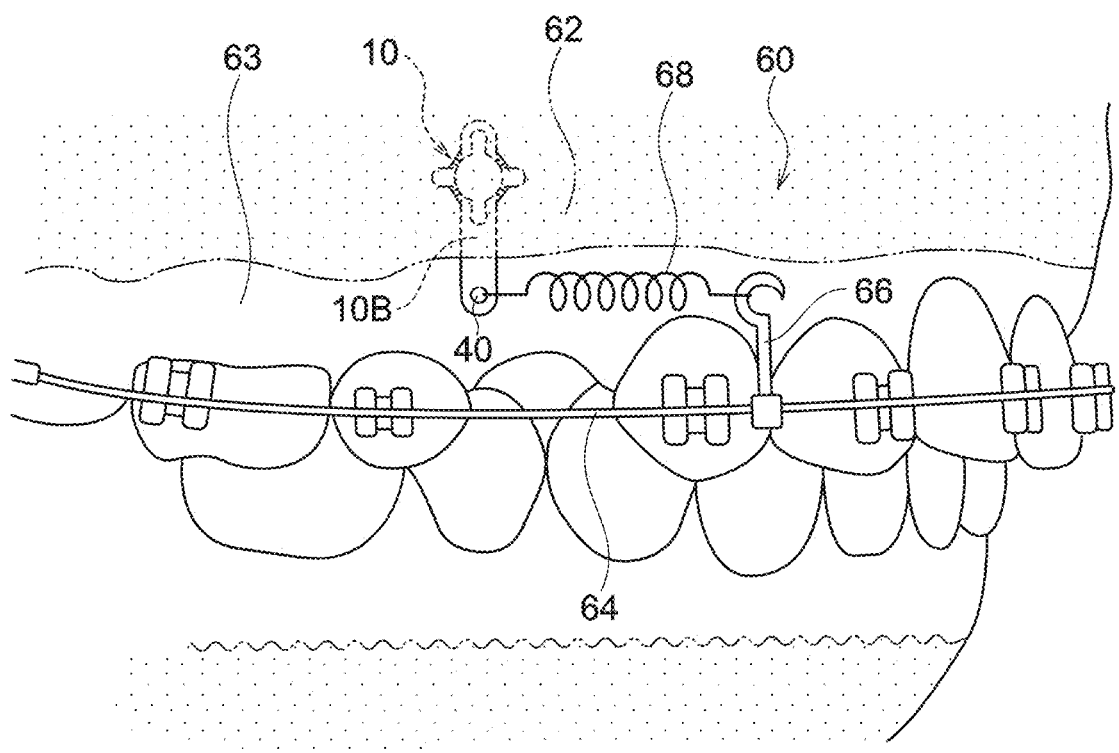
FIG. 5 is a front view showing a device structure for dentistry according to a third exemplary embodiment of the present invention, illustrating an example in which the device shown in FIG. 1 is used for orthodontics.

Now, a third exemplary embodiment of the medical device according to the present invention, which is a device structure for dentistry, is described using FIG. 5. Structural elements, members and the like of the third exemplary embodiment that are the same as in the first and second exemplary embodiments are assigned the same reference numerals and are not described in detail.

FIG. 5 shows a device structure for dentistry 60, which is an example in which the device 10 shown in FIG. 1 is used for orthodontics. As shown in FIG. 5, in the device structure for dentistry 60, the shaft portion 10A of the device 10 (see FIG. 1) is inserted into the bone 20 at the inner side of an alveolar mucous membrane 62 (see FIG. 3C; between teeth in the present exemplary embodiment). The shaft portion 10A of the device 10 is inserted into the cortical bone 22 of the bone 20, or is inserted through the cortical bone 22 of the bone 20 to a position reaching the cancellous bone 24 (see FIG. 3D and the like). In the present exemplary embodiment, the main body of the device 10 is covered by the alveolar mucous membrane 62, but one of the inflected portions 10B is extended so as to protrude to the outer side of a boundary region between the alveolar mucous membrane 62 and an attached gum 63. A hole 40 that is separate from the aperture portion 16 is provided at an end portion of the extended inflected portion 10B. Various devices developed for orthodontic treatments may be disposed at the hole 40. In the present exemplary embodiment, the device 10 and a hook 66 connected to an orthodontic archwire 64 are connected by a spring 68. Consequently, the device 10 is used as an anchorage for teeth movement.

In this device structure for dentistry 60, the axial direction length of the shaft portion 10A of the device 10 is set to around 2.0 mm, which is shorter than an axial direction length of a conventional orthodontic implant or the like (for example, around 10 mm or more). Therefore, in the device structure for dentistry 60, because the device 10 is used as an anchorage for teeth movement, damage to a tooth root, tooth germ or the like may be suppressed more effectively than with a conventional orthodontic implant or the like in which around 5 mm or more of a shaft portion is inserted into cancellous bone. Thus, the device structure for dentistry 60 has minimal invasion into the patient. In the device structure for dentistry 60, cells with a bone-forming function migrate from inside the bone through the shaft portion 10A with the hollow shape of the device 10, and new bone is formed at the inner face side of the shaft portion 10A by these cells. As a result, firm bonding of the device 10 with the bone 20 may be realized.

In the device structure for dentistry 60 according to the present exemplary embodiment, a position of the bone 20 at which the shaft portion 10A of the device 10 is inserted is not limited to the position illustrated in FIG. 5 and may be modified.

The devices according to the first exemplary embodiment and the second exemplary embodiment are not limited to orthodontic applications. For example, these devices may be used for applications such as various devices for orthopedic surgery, otorhinolaryngology and the like, for an epithese in head and neck surgery, and so forth. The term "epithese" refers to an artificial object attached to a surface of the body to be used as a medical device. When, for example, a device according to the first exemplary embodiment or second exemplary embodiment is used for an orthopedic purpose, the thickness of the cortical bone a bone is thicker than in orthodontics. Therefore, it is preferable if the axial direction length of the shaft portion of the device is lengthened to suit the thickness of the cortical bone.

In the third exemplary embodiment, the device structure for dentistry 60 is illustrated with the device being applied to an orthodontic treatment, but the present invention is not limited thus. For example, the present invention may be applied to device structures to be used in fixing devices to bone at other areas of the teeth, areas of head and neck surgery, and areas of orthopedic surgery.

EXAMPLE

Below, an Example is given and the present invention is described in more concrete terms. The scope of the present invention is not to be understood as being limited by the specific Example illustrated below.

<1> Fabrication of a Device (Pin Device)

A tube fabricated of pure titanium was used as a metal base material. In specific terms, a tube fabricated of pure titanium with an outer diameter of 2.4 mm, a plate thickness of 0.25 mm and a length of 10 mm was cut and used. The titanium tube was formed into the device (pin device) 10 shown in FIG. 1 using a diamond wheel saw, a round bur and pliers. As shown in FIG. 1, the device 10 was provided with the shaft portion 10A in the hollow shape and the plural inflected portions (outer flaps) 10B and 10C inflected to the radial direction outer sides from the one end portion of the axial direction of the shaft portion 10A. Four of the slits 14 along the axial direction were formed at the shaft portion 10A. The aperture portions 16 were provided at the pair of inflected portions 10B; no aperture portions were provided at the other pair of inflected portions 10C. The device (pin device) was cleaned with ultrasound for 30 minutes in each of, successively, a neutral detergent, purified water, acetone, ethanol, and purified water. The device was then sterilized with an autoclave and was used in an animal experiment.

<2> Animal Experiment

Figures 6A, 6B:
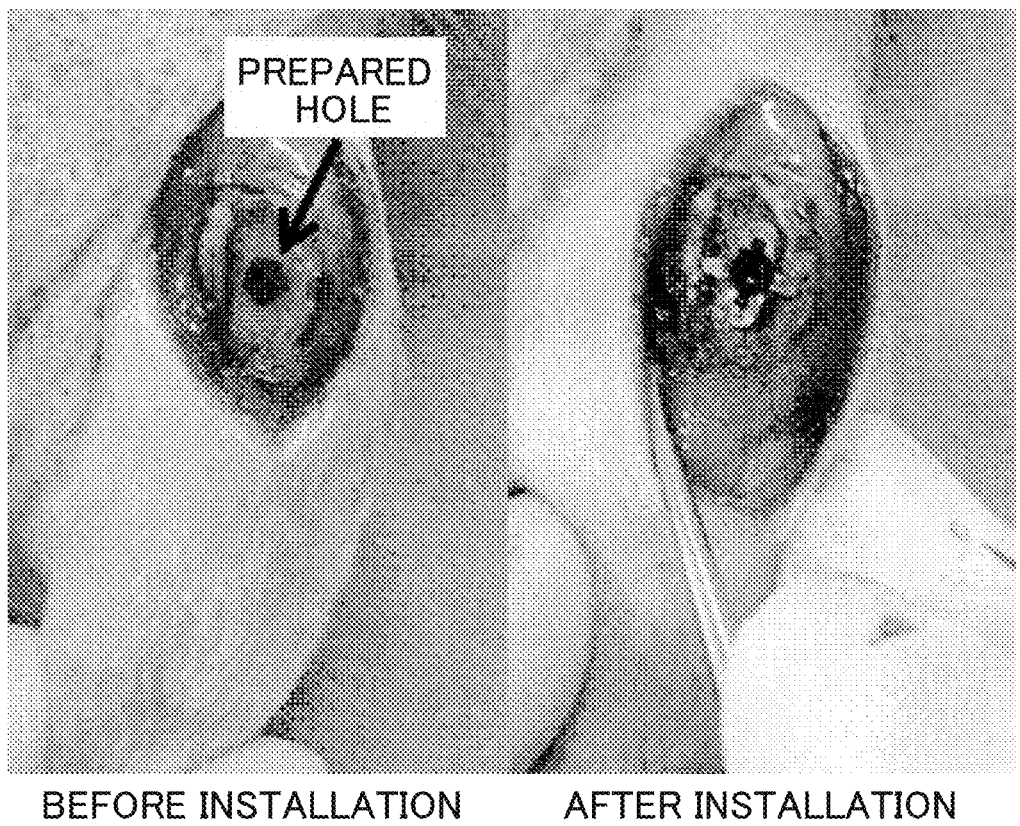
FIGS. 6A and 6B are photographs showing states before and after a device according to an Example is installed in cortical bone in the tibia of a rat.

At the inner side of the tibia at a knee joint of a 12-week-old male Sprague Dawley rat, a prepared hole with a diameter of 2.2-2.3 mm and a depth of 3 mm was formed (FIG. 6A) with a round bur, and the device was installed in the prepared hole (FIG. 6B). At this time, the pair of inflected portions 10B with the aperture portions 16 were arranged in the length direction of the tibia. The device was installed to penetrate through cortical bone with the distal end reaching cancellous bone (mono-cortical fixing).

Four weeks after the installation of the device, the device and the tibia were harvested together, and a histological examination and mechanical test were carried out.

The histological examination, to examine bone structure around the device, was carried out by micro-computed tomography. Micro-computed tomography imaging was carried out using an SMX100CT, manufactured by SHIMADZU CORPORATION, and images were reproduced with the 3D-BON image analysis software, from RATOC SYSTEM ENGINEERING CO., LTD.

The mechanical test, to check the bonding strength to bone of the device, was carried out using an AG-X universal testing machine manufactured by SHIMADZU CORPORATION. The device was harvested together with the tibia, stored in physiological saline solution at 4° C., and tested within one hour. A wire was passed through the aperture portion 16 (see FIG. 1) of the inflected portion 10B of the device that was at the knee joint side of the tibia, and a tension force was applied parallel to the long axis direction of the tibia. At this time, bone around the inflected portion 10B of the device to which the wire was to be applied (FIG. 1) was removed with a round bur (FIGS. 7A and 7B).

Figure 8:
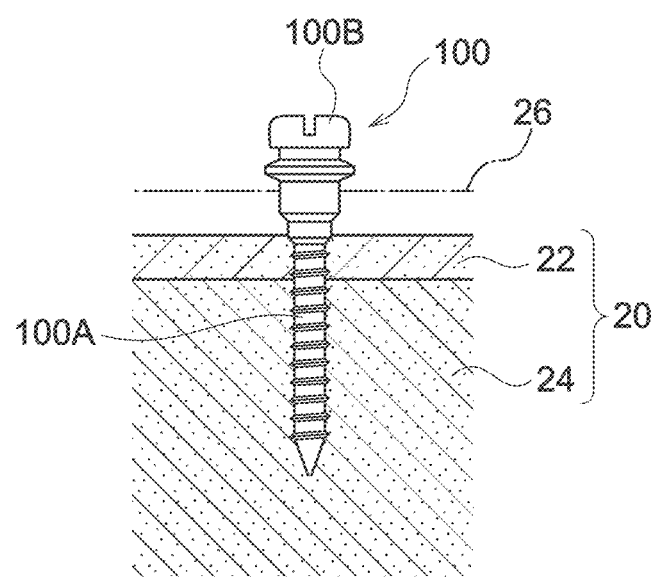
FIG. 8 is a sectional diagram showing a state in which an orthodontic anchor screw according to a Comparative Example is fixed to bone.
Figure 9A:
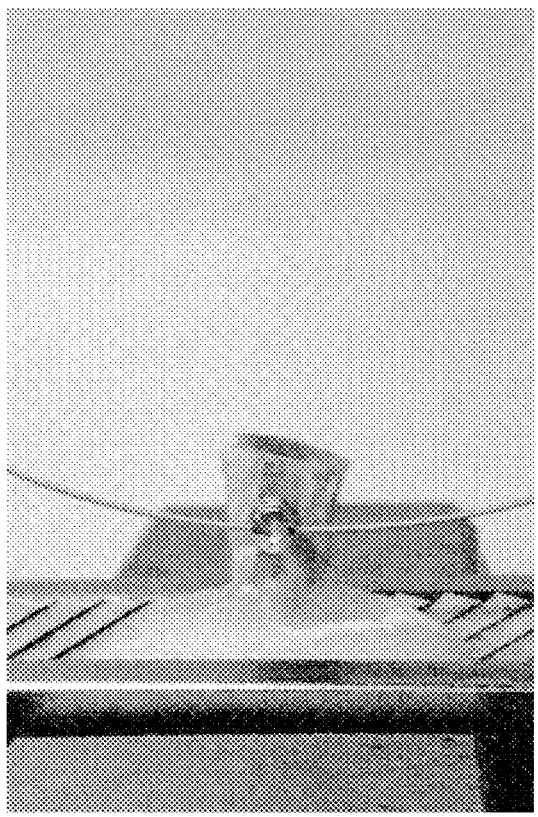
FIGS. 9A and 9B are photographs showing schematics of a mechanical test to check a bonding strength to bone of the orthodontic anchor screw shown in FIG. 8.
Figure 9B:
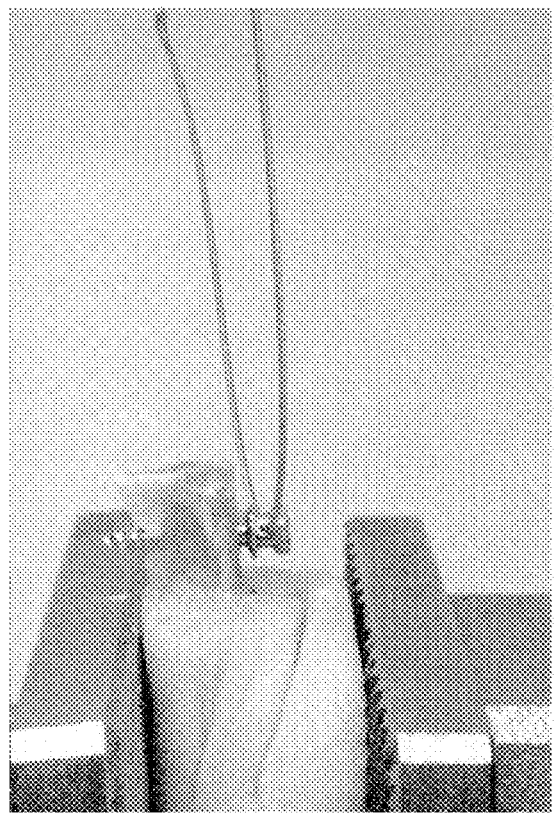

As a comparison for the bonding strength to bone, the same mechanical test was carried out using a conventional orthodontic anchor screw illustrated in FIG. 8. As shown in FIG. 8, an orthodontic anchor screw 100 was provided with a shaft portion 100A with a solid shape and a head portion 100B at one end portion of the axial direction of the shaft portion 100A. The shaft portion 100A was provided with a screw ridge at an outer periphery face thereof. The head portion 100B had a larger outer diameter than the shaft portion 100A. The orthodontic anchor screw that was used had a diameter of 2.0 mm and a length of 8.0 mm. For reference, an insertion location of the orthodontic anchor screw was fixed at a position of the knee joint that was at the same position as the device. In order to avoid damage to the tibia when the orthodontic anchor screw was inserted, a prepared hole was formed at the cortical bone by a round bur with a diameter of 1.2 mm, and the anchor screw was inserted (see FIGS. 9A and 9B) so as to penetrate through the tibia (bi-cortical fixing). A wire was passed through a hole formed at the head portion of the orthodontic anchor screw, and the mechanical test was carried out in the same manner as for the device (FIGS. 9A and 9B).

<3> Results

Figure 10A:
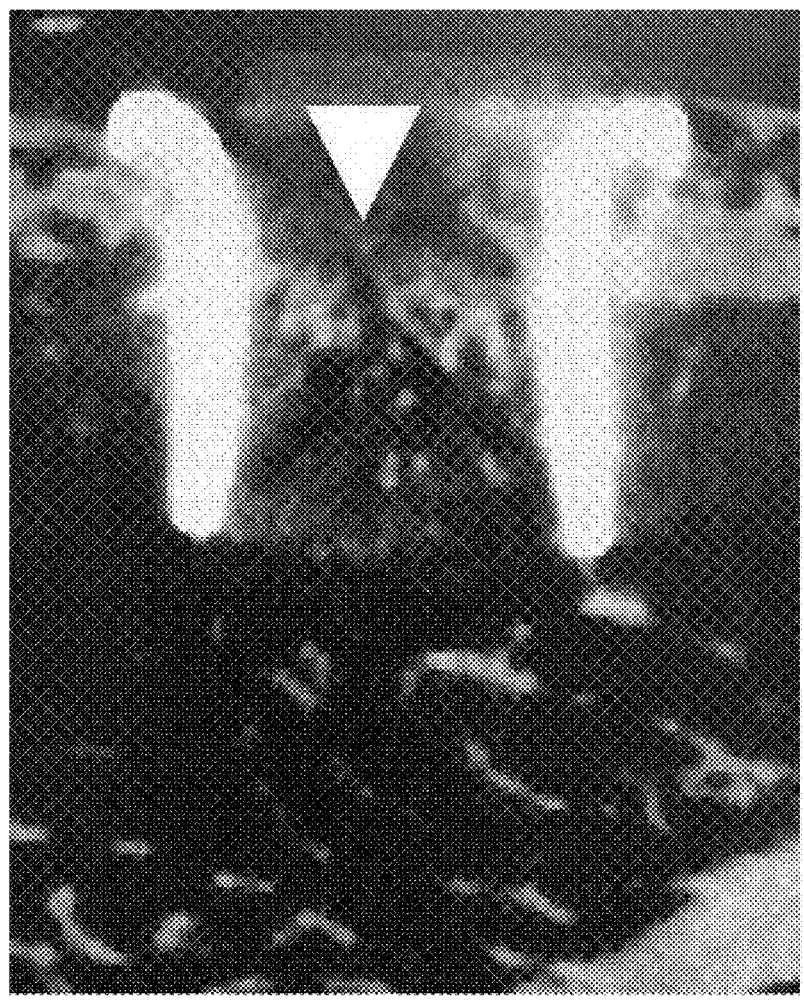
FIG. 10A is an image (an image reconstructed from micro-computed tomography) showing bone structure around the device according to the Example.

Images of bone structure around the device (images reconstructed from micro-computed tomography) are shown in FIGS. 10A and 10B(i), (ii), and (iii). As seen in FIG. 10A, the formation of new bone at the inner face side of the shaft portion of the device was confirmed (see the arrowhead). The formation of new bone over the whole of the inner face side of the shaft portion of the device was not observed; only a range in the depth direction of around the same depth as the surrounding cortical bone was observed. In FIGS. 10B (i), (ii), and (iii), the middle image (FIG. 10B(ii)) corresponds to a section of a region of the horizontal line in the lower image (FIG. 10B(iii)). As seen in the middle image (FIG. 10B(ii)), the formation of new bone in the aperture portions of the inflected portions was confirmed (see the arrow in the middle image (FIG. 10B(ii)). The upper image (FIG. 10B(i) corresponds to a section of a region of the diagonal line in the lower image (FIG. 10B(iii). As seen in the upper image (FIG. 10B(i)), the formation of new bone between the inflected portions was confirmed (see the arrowheads in the upper image (FIG. 10B(i))).

Results of the mechanical test are shown in FIG. 11. The maximum strengths found in the mechanical test (the arrowed positions in the graph) were 48.7 N for the device and 37.8 N for the orthodontic anchor screw. This test showed that the device had a bonding strength around 10 N higher even though the device had mono-cortical fixing and the orthodontic anchor screw had bi-cortical fixing, a condition that was advantageous for the anchor screw.

From the results described above, it can be seen that with the device according to the present invention, new bone was formed at the inner face side of the shaft portion of the device in the four weeks after installation in the bone, and the device provided a stronger bonding strength to bone than the conventional orthodontic anchor screw.

Fourth Exemplary Embodiment

Figure 12A:
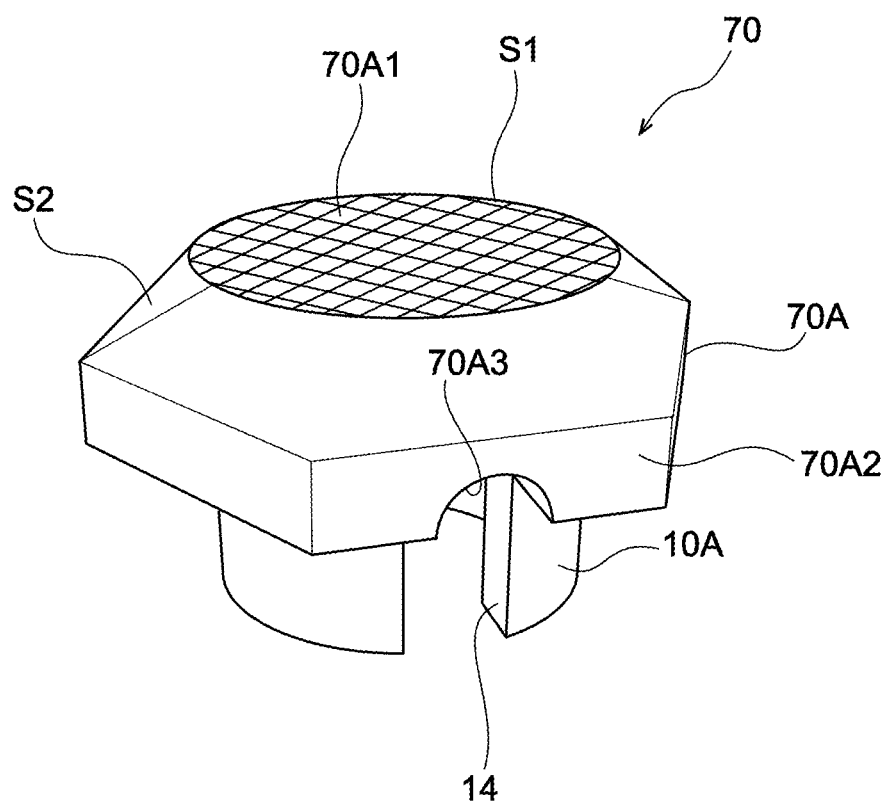
FIG. 12A is a perspective view showing a device that serves as a medical device according to a fourth exemplary embodiment of the present invention.
Figure 12B:
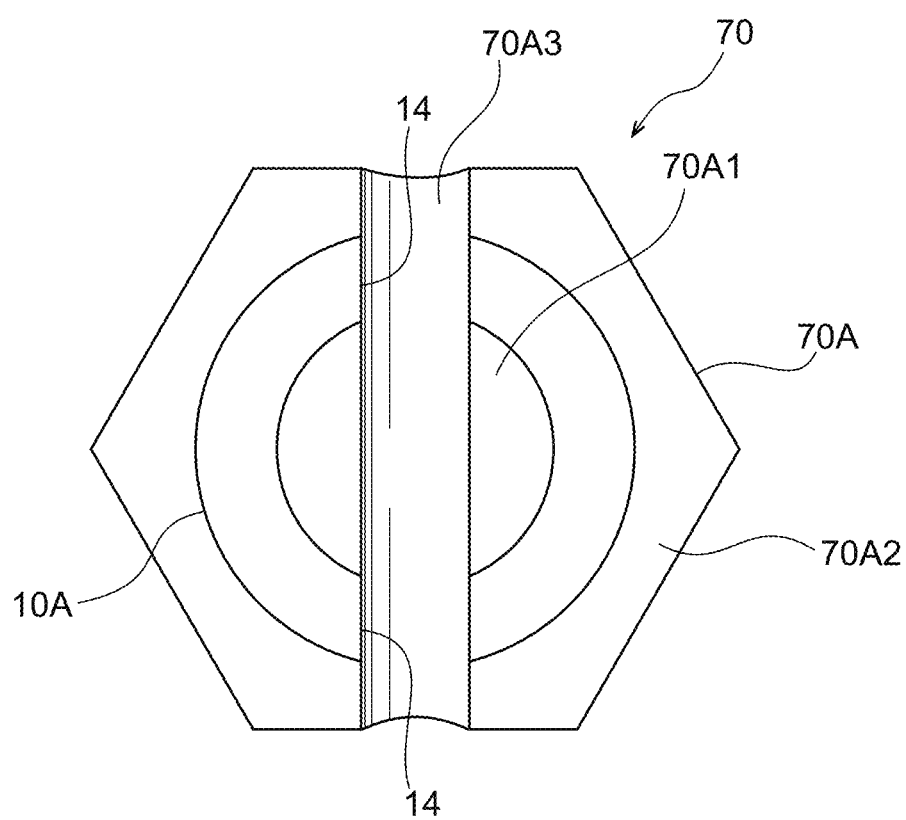
FIG. 12B is a bottom view showing the device shown in FIG. 12A.

Now, a fourth exemplary embodiment of the medical device according to the present invention is described using FIG. 12A to FIG. 12C. Structural elements, members and the like of the fourth exemplary embodiment that are the same as in the first and second exemplary embodiments are assigned the same reference numerals and are not described in detail.

As shown in FIG. 12A and FIG. 12B, a device 70 (a medical device) is provided with the shaft portion 10A with the hollow shape. An outer periphery face of the shaft portion 10A is formed in a cylindrical surface shape. Two of the slits 14 are formed at the shaft portion 10A. The two slits 14 are disposed to be spaced by 180° along the circumferential direction of the shaft portion 10A.

A head portion 70A that serves as an exposed portion is provided at one end portion of the axial direction of the shaft portion 10A. Viewed in the axial direction of the shaft portion 10A, the head portion 70A is formed in a hexagonal shape. The head portion 70A is provided with a closed portion 70A1 that closes off the open end of the shaft portion 10A and with an outer periphery side extended portion 70A2 that extends from the closed portion 70A1 to outer sides in radial directions of the shaft portion 10A. Of the closed portion 70A1 and the outer periphery side extended portion 70A2, the surface of a region of the closed portion 70A1 at the opposite side thereof from the side at which the shaft portion 10A is disposed serves as a flat surface S1 that extends in the radial directions of the shaft portion 10A. A surface roughness of the flat surface S1 is adjusted to a predetermined roughness by the application of mechanical processing or the like to the flat surface S1. To be more specific, the surface roughness of the flat surface S1 is adjusted such that adherence of an adhesive to the flat surface S1 will be excellent. The surface roughness of the flat surface S1 may be adjusted by the application of filing, shot blasting or the like.

A surface of the outer periphery side extended portion 70A2 at the opposite side thereof from the side at which the shaft portion 10A is disposed serves as an angled surface S2, which is angled to be closer to the shaft portion 10A toward the outer sides in the radial directions of the shaft portion 10A.

A recessed groove portion 70A3 that opens toward the shaft portion 10A is formed at an end portion of the head portion 70A at the side thereof at which the shaft portion 10A is disposed. The recessed groove portion 70A3 penetrates through the head portion 70A and is linked with the two slits 14 formed at the shaft portion 10A.

As shown in FIG. 12C, similarly to the device 10 according to the first exemplary embodiment (see FIG. 3B), the hole portion 28 is formed at the bone 20 to be smaller than the outer diameter of the shaft portion 10A, after which the shaft portion 10A of the device 70 is inserted into the hole portion 28 in the bone 20. In the present exemplary embodiment, the shaft portion 10A may be inserted into the hole portion 28 in the bone 20 by a tool that corresponds with the shape of the head portion 70A (the hexagonal shape) being engaged with the head portion 70A. Thus, the shaft portion 10A is fixed to the bone 20.

A thickness of the head portion 70A and the like are specified such that, in the state in which the device 70 according to the present exemplary embodiment is fixed to the bone 20, the flat surface S1 of the head portion 70A of the device 70 is exposed from the mucous membrane 26 that is the epithelium covering the bone 20 (the cortical bone 22 (see FIG. 3C)). Hence, another medical device or the like may be joined to the flat surface S1 of the head portion 70A by an adhesive or the like. This other medical device may be, for example, the spring 68 and hook 66 described in the third exemplary embodiment (see FIG. 5).

In the present exemplary embodiment, the cells with the bone-forming function migrate through the interior of the shaft portion 10A with the hollow shape of the device 70 to the recessed groove portion 70A3, and new bone is formed inside the recessed groove portion 70A3. Thus, the device 70 and the bone 20 may be more firmly joined. Therefore, the device 70 may be firmly joined to the bone 20 even with the short shaft portion 10A.

Fifth Exemplary Embodiment

Figure 13A:
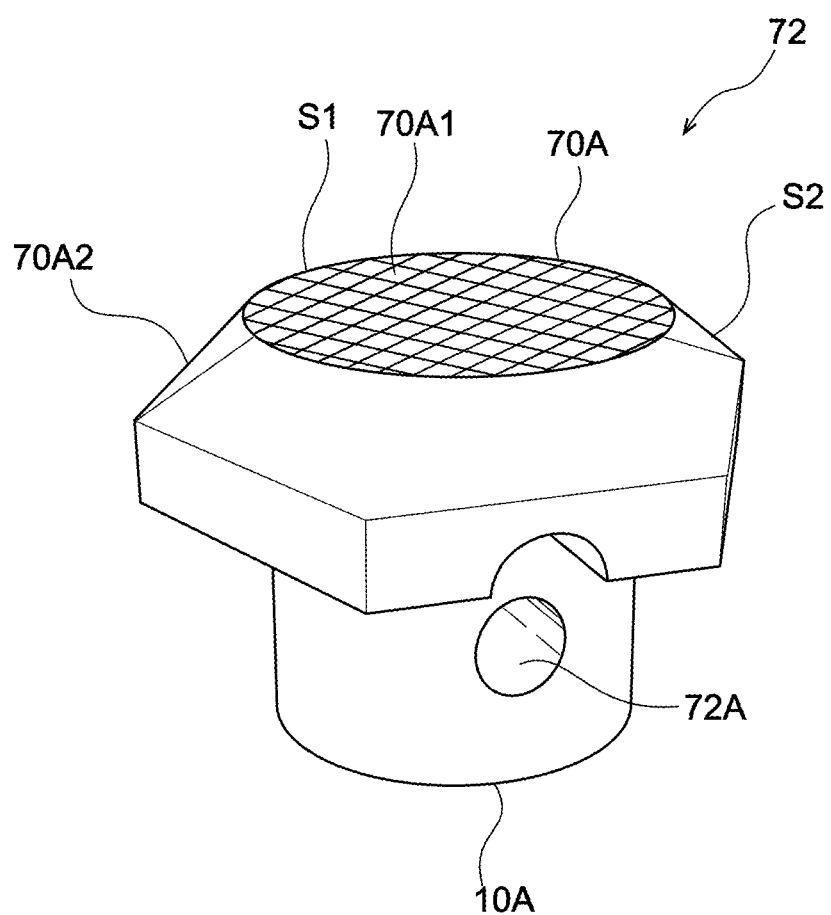
FIG. 13A is a perspective view showing a device that serves as a medical device according to a fifth exemplary embodiment of the present invention.
Figure 13B:
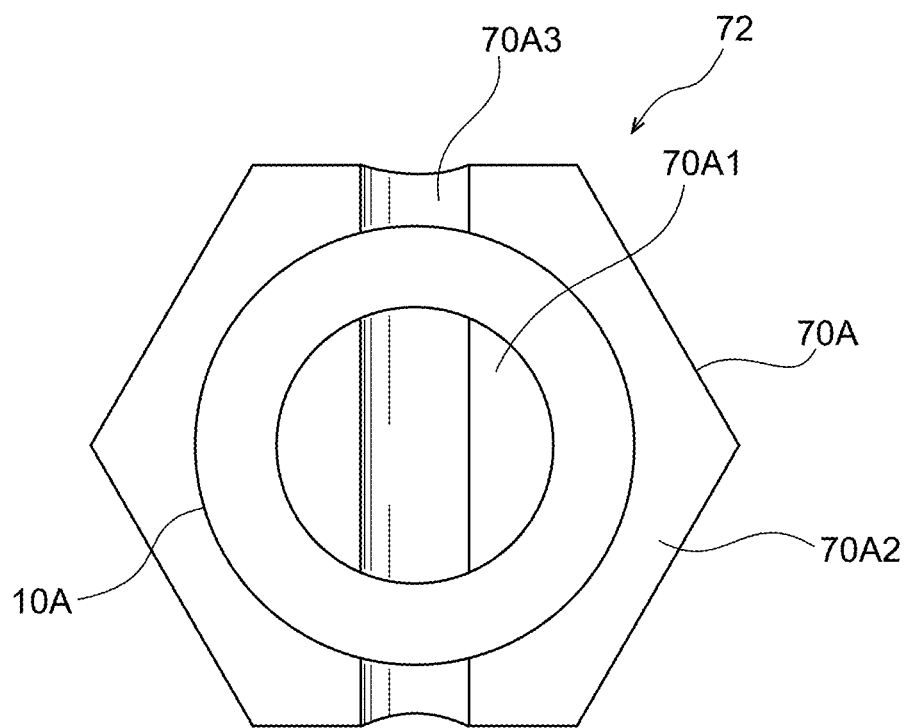
FIG. 13B is a bottom view showing the device shown in FIG. 13A.
Figure 13C:
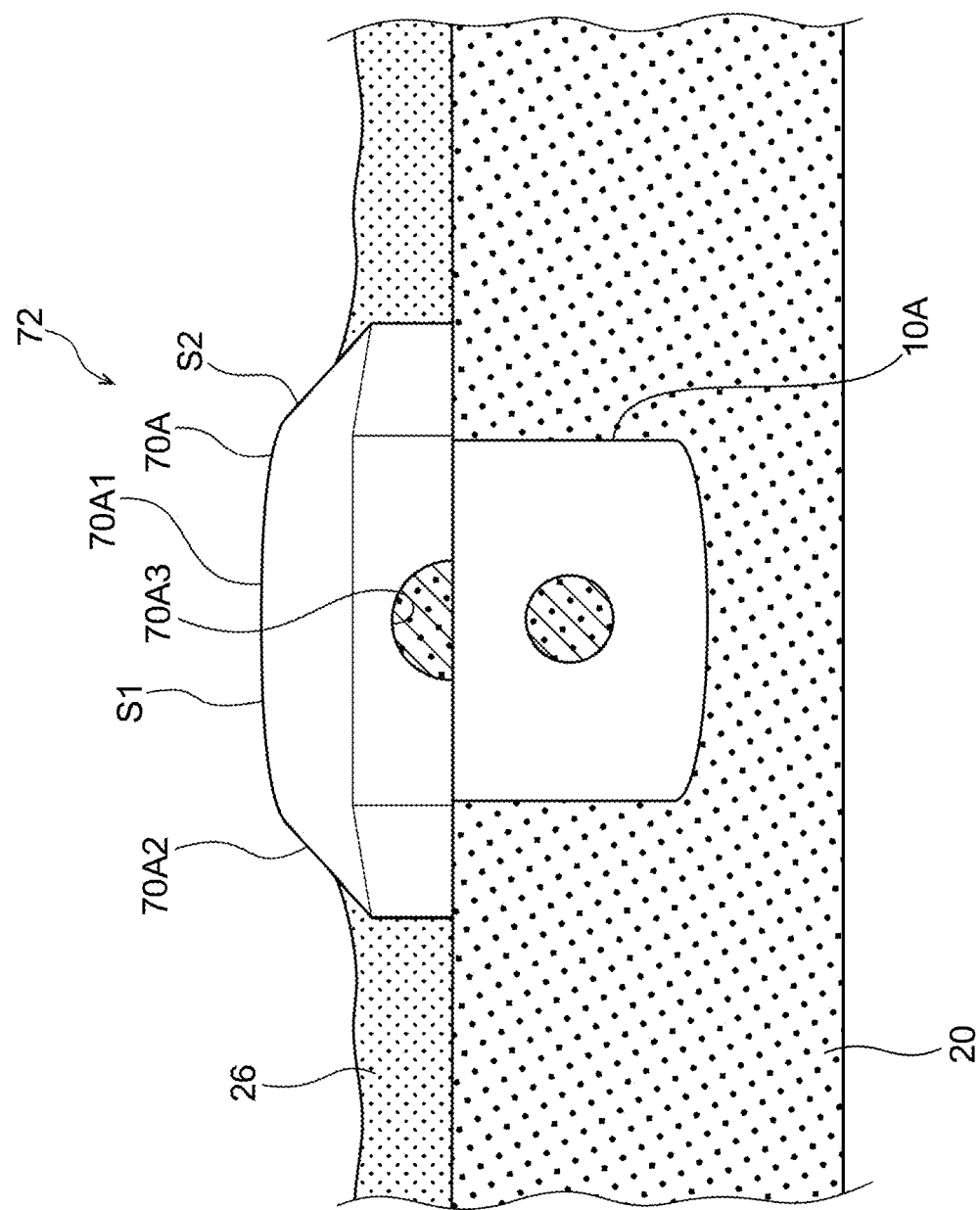
FIG. 13C is a sectional diagram showing a state in which the device shown in FIG. 13A is joined to bone.

Now, a fifth exemplary embodiment of the medical device according to the present invention is described using FIG. 13A to FIG. 13C. Structural elements, members and the like of the fifth exemplary embodiment that are the same as in the first to third exemplary embodiments are assigned the same reference numerals and are not described in detail.

As shown in FIG. 13A and FIG. 13B, in a device 72 (a medical device) according to the present exemplary embodiment, a circular penetrating hole 72A is formed at the shaft portion 10A instead of the slits 14 that are formed at the shaft portion 10A of the device 70 according to the fourth exemplary embodiment (see FIG. 12A). The penetrating hole 72A penetrates through the shaft portion 10A in a direction orthogonal to the axial direction of the shaft portion 10A. In addition, the recessed groove portion 70A3 is formed in communication with the cavity at the diametric direction inner side of the shaft portion 10A. As shown in FIG. 13C, according to this device 72, the cells with the bone-forming function may migrate through the penetrating hole 72A and the recessed groove portion 70A3. Thus, a portion (of new bone) that links the bone 20 outside the shaft portion 10A with the new bone formed inside the shaft portion 10A may be formed at peripheral edge portions of the penetrating hole 72A. Therefore, the device 72 and the bone 20 may be more firmly joined and rotation of the device 72 may be suppressed. In the present exemplary embodiment, an example is described in which the penetrating hole 72A is formed instead of the slits 14, but the present invention is not limited thus. For example, a structure is possible in which the slits 14 and the penetrating hole 72A are both formed at the shaft portion 10A.

While a number of representative embodiments of the present invention have been described hereabove, the present invention is not to be limited by these embodiments. The scope of the present invention is to be defined only by the scope of the claims below.

The invention claimed is:

1. A medical device comprising:
   a hollow shaft portion with a shape configured to be inserted into a cortical bone or the hollow shaft portion penetrating through the cortical bone and inserted to a position reaching a cancellous bone at an inner side of the cortical bone, the entire hollow shaft portion being hollow, within and from which cells with a bone-forming function can migrate;
   at least one first inflected portion that is integrally inflected in a radial direction outwardly from one end portion of the hollow shaft portion and extends beyond an external surface of the hollow shaft portion, the at least one first inflected portion being configured to be exposed at a surface of the cortical bone when said hollow shaft portion is inserted into or through the cortical bone;
   at least one slit extending over a whole length of the hollow shaft portion in an axial direction, one end of the at least one slit having an opening at an end of the hollow shaft portion distal from the at least one first inflected portion, and an outer diameter of the hollow shaft portion being configured to deform in directions of expansion and contraction;
   an aperture portion provided at a location of the at least one first inflected portion that is adjacent to the hollow shaft portion and continuous with an associated at least one slit, the aperture portion being closed at a radial end of the at least one first inflected portion, wherein cells with a bone-forming function are configured to migrate from inside the cortical bone through the at least one slit and the opening, and new bone is configured to be formed by the cells at an inner face side space of the hollow shaft portion and at an area over and around the at least one first inflected portion, promoting bonding to the bone; and,
   at least one second inflected portion that is integrally inflected in a radial direction outwardly from one said end portion of the hollow shaft portion and extends outwardly beyond the external surface of the hollow shaft portion, the at least one second inflected portion being configured to be exposed at a surface of the cortical bone when said hollow shaft portion is inserted into or through the cortical bone, wherein an aperture portion is not provided at said at least one second inflected portion.

2. The medical device according to claim 1, comprising a plurality of first inflected portions and/or second inflected portions provided in a circumferential direction of the hollow shaft portion.

3. The medical device according to claim 1, wherein a length of the hollow shaft portion in the axial direction is specified such that at least 70% of the length is disposed in the cortical bone when said hollow shaft portion is inserted into or through the cortical bone.

4. The medical device according to claim 1, wherein a male thread portion is provided at an outer periphery face of the hollow shaft portion.

5. The medical device according to claim 1, wherein the hollow shaft portion and at least one first inflected portion and/or at least one second inflected portion are formed of titanium or titanium alloy.

6. The medical device according to claim 1, wherein a surface of the hollow shaft portion and at least a portion of at least one first inflected portion and/or at least one second inflected portion is coated with a biofunctional material.

7. A device structure for dentistry, for head and neck surgery or for orthopedic surgery, comprising the medical device according to claim 1, the device structure employing the medical device to fix the device structure to the bone.

8. A method for bonding the medical device according to claim 1 to a bone, the method comprising:
- a step of fixing the hollow shaft portion to the bone in a state in which the hollow shaft portion is inserted into the cortical bone or the hollow shaft portion penetrates through the cortical bone and is inserted to the position reaching the cancellous bone at the inner side of the cortical bone, and in a state in which the at least one first inflected portion is exposed at the surface of the cortical bone, and
- allowing cells with a bone-forming function to migrate from inside the bone through the shape of the hollow shaft portion and the at least one slit, allowing bone to be formed by the cells at an inner face side of the hollow shaft portion, and promoting bonding of the medical device to the bone.

9. The medical device according to claim 1, wherein the at least one first inflected portion and/or at least one second inflected portion comprises a plurality of inflected portions provided in a circumferential direction of the hollow shaft portion.

10. The medical device according to claim 1, wherein the inner face side space of the hollow shaft portion is inserted by a material promoting the bone-forming function.

11. A medical device for orthodontic dentistry comprising:
- a hollow shaft portion with a shape configured to be inserted into a cortical bone or the hollow shaft portion penetrating through the cortical bone and inserted to a position reaching a cancellous bone at an inner side of the cortical bone, the entire hollow shaft portion being hollow, within and from which cells with a bone-forming function can migrate;
- an exposed portion that includes at least one outer periphery side extended portion that integrally extends to a radial direction outer side from one end portion of an axial direction of the hollow shaft portion, the exposed portion being exposed at a surface of the cortical bone, the one end portion of the hollow shaft portion being completely closed off by the exposed portion and free of axial openings, and at least a portion of a surface at a side of the exposed portion opposite from the side thereof at which the hollow shaft portion is disposed is to be exposed from an epithelium that covers the cortical bone when said hollow shaft portion is inserted into or through the cortical bone, wherein a flat surface that extends in radial directions of the hollow shaft portion is formed integrally at an opposite side of the closed portion of the exposed portion that faces the hollow shaft portion; and
- at least one slit extending over a whole length of the hollow shaft portion in the axial direction, one length direction end of the at least one slit having an opening at a distal end of the hollow shaft portion at an opposite side of the at least one extending portion, and an outer diameter of the hollow shaft portion being configured to deform in directions of expansion and contraction, wherein cells with a bone-forming function are configured to migrate from inside the cortical bone through the at least one slit, and new bone is configured to be formed by the cells at an inner face side space of the hollow shaft portion, promoting bonding to the bone.

12. The medical device according to claim 11, wherein a groove is provided at a location of a floor face of the exposed portion that is adjacent to the hollow shaft portion, the groove being linked with the at least one slit, opening at an inner face of the hollow shaft portion, or a combination thereof.

* * * * *